(12) United States Patent
Bader

(10) Patent No.: US 10,464,831 B1
(45) Date of Patent: *Nov. 5, 2019

(54) TREATMENT OF PRODUCED WATER FROM UNCONVENTIONAL SOURCES OF HYDROCARBONS

(71) Applicant: Mansour S. Bader, College Station, TX (US)

(72) Inventor: Mansour S. Bader, College Station, TX (US)

(*) Notice: Subject to any disclaimer, the term of this patent is extended or adjusted under 35 U.S.C. 154(b) by 156 days.

This patent is subject to a terminal disclaimer.

(21) Appl. No.: 15/732,033

(22) Filed: Sep. 7, 2017

Related U.S. Application Data

(63) Continuation-in-part of application No. 14/545,681, filed on Jun. 6, 2015, now Pat. No. 9,751,777.

(51) Int. Cl.
| | |
|---|---|
| C02F 1/52 | (2006.01) |
| C02F 1/58 | (2006.01) |
| C07C 211/03 | (2006.01) |
| C09K 8/36 | (2006.01) |
| C02F 1/62 | (2006.01) |
| E21B 43/26 | (2006.01) |

(52) U.S. Cl.
CPC ............ *C02F 1/5272* (2013.01); *C02F 1/586* (2013.01); *C02F 1/62* (2013.01); *C07C 211/03* (2013.01); *C09K 8/36* (2013.01); *E21B 43/26* (2013.01)

(58) Field of Classification Search
USPC ................................. 210/638; 95/92; 202/152
See application file for complete search history.

(56) References Cited

U.S. PATENT DOCUMENTS

| | | | | |
|---|---|---|---|---|
| 5,035,807 | A * | 7/1991 | Maree | C02F 1/20 210/711 |
| 5,403,483 | A * | 4/1995 | Hayashida | B01D 39/083 210/490 |
| 6,365,051 | B1 | 4/2002 | Bader | |
| 6,663,778 | B1 | 12/2003 | Bader | |
| 7,093,663 | B1 | 8/2006 | Bader | |
| 7,501,065 | B1 | 3/2009 | Bader | |
| 7,789,159 | B1 | 9/2010 | Bader | |
| 7,934,551 | B1 | 5/2011 | Bader | |
| 7,963,338 | B1 | 6/2011 | Bader | |
| 8,197,696 | B1 | 6/2012 | Bader | |
| 8,915,301 | B1 * | 12/2014 | Bader | C02F 9/00 166/371 |
| 8,961,916 | B1 | 2/2015 | Bader | |
| 9,701,558 | B1 | 7/2017 | Bader | |
| 9,751,777 | B1 * | 9/2017 | Bader | C02F 1/40 |
| 2007/0102359 | A1 * | 5/2007 | Lombardi | B01D 17/085 210/639 |
| 2009/0277797 | A1 * | 11/2009 | Pruet | B03C 9/00 205/162 |
| 2012/0234765 | A1 * | 9/2012 | Sengupta | B01J 39/02 210/670 |

(Continued)

*Primary Examiner* — Nina Bhat

(57) ABSTRACT

There is provided herein a system and method to effectively treat produced water. In some embodiments, produced water is treated by mixing produced water with an amine solvent and humic acid to form precipitates comprising magnesium, strontium, barium and radium hydroxides in a precipitator unit. Precipitates are then removed by a filter to produce de-scaled produced water. The amine solvent is recovered from the de-scaled produced water by a stripping unit.

25 Claims, 15 Drawing Sheets

(56) References Cited

U.S. PATENT DOCUMENTS

| | | | |
|---|---|---|---|
| 2013/0118994 A1* | 5/2013 | Altman | C02F 1/463 210/748.12 |
| 2013/0270187 A1* | 10/2013 | Seibert | B01D 63/02 210/644 |
| 2014/0008271 A1* | 1/2014 | Moene | B01D 17/0214 208/188 |
| 2015/0083669 A1* | 3/2015 | Matherly | C02F 1/5236 210/723 |
| 2016/0040522 A1* | 2/2016 | Jacob | E21B 43/20 166/267 |
| 2016/0176735 A1* | 6/2016 | Balasubramanian | C02F 1/50 210/729 |

* cited by examiner

*Configuration A:*

*Configuration B:*

TREATMENT OF PRODUCED WATER FROM UNCONVENTIONAL SOURCES OF HYDROCARBONS

A RELATED APPLICATION

This application is a continuation-in-part of my patent application Ser. No. 14/545,681 filed on Jun. 6, 2015, now U.S. Pat. No. 9,751,777.

BACKGROUND OF THE INVENTION

Unconventional hydrocarbons production from low-permeability organic-rich shale and tight-sand formations is rapidly expanding. It opens vast new energy sources to the nation. Gas productions in 2012 from shale and tight-sand formations were, respectively, accounting for 34% and 24% of the nation's total gas production. Unconventional gas production is currently dominant in Marcellus Basin (29%), Haynesville Basin (23%), Barnett Basin (17%), and the remaining 31% is contributed by about 20 other basins. Future forecasts indicate that unconventional gas production will double by 2035 whereas unconventional oil production will increase by about 15%.

However, unconventional hydrocarbons exploration may impose adverse health and environmental long-term effects. In shale and tight-sand exploration, a fluid is used to fracture and stimulate the formation. This fluid is referred to as fracturing fluid or completion fluid. Fracturing fluid is typically potable water mixed with a large number of additives, and some of which are toxic chemicals. The average required volume of fracturing fluid is about 40,000 barrels for a vertical well and 100,000 barrels for a horizontal well.

The fluid that flows back during and after fracturing is often denoted flow-back water (FBW) or produced water (PW). However, it is referred to in this invention as PW. A portion of the fracturing fluid (e.g., 20-45%) flows back to the surface as PW, and the flow of PW substantially decreases with time to near halation at the well completion (30-90 days). During fracturing, ions including alkaline cations (magnesium, calcium, strontium, barium and radium), Naturally Occurring Radioactive Materials (NORM; the decay series of radium), and transition metals within formation layers are dissolved, mixed with high salinity formation water, and mobilized to the surface with PW. As such, ions concentrations in PW sharply increase with time; the longer the downhole residence time, the higher their concentrations in PW. Table 1 [Haluszczak, L. O., et al., Applied Geochemistry, 2013, 28, pp. 55-61] and Table 2 [Hayes, T. and Severin, B. F., RPSEA Final Report #08122-05, 2012], for example, present some samples of PW at 10-14 days from, respectively, Marcellus and Barnett basins. Alkaline cations (magnesium, calcium, strontium, barium and radium), particularly radium radioactive isotopes, along with bromide are signatures for such PW.

Hydro-fracturing is thus faced with surmounted predicaments driven by negative public perception for several reasons. First, the 2005 Energy Policy Act exempts fracturing operations from the Safe Drinking Water Act (SDWA) with one exception (injection of diesel) to the exemption. Health and environmental regulations, monitoring, and enforcement for various contaminants by individual states were moot. Such, due to public pressure, are now continually evolving, which focus on the disclosure of the constituents in fracturing fluids as well as in PW (discharge and reuse of PW). One of the critical moves is the development of appropriate analytical methods, particularly for radioactivity, to replace the "drift" of extending existing analytical procedures, which may not be applicable (e.g., outdated) to such PW and tend to underestimate the levels of some critical contaminants.

Second, the toxic-nature of fracturing fluids as well as the toxic- and possible radioactive-nature of PW are alarming. The journey of fracturing fluids from the surface to downhole formation and back to the surface with carried over PW may contaminate groundwater aquifers via geological connectivity and leakage. Also, of concern is leakage from PW holding ponds.

Third, the common method to manage PW is of course disposal in deep wells. However, the demand for such disposal wells is overwhelming due to the sheer volume of PW. For example, PW from the Marcellus basin was over 31 million barrels in 2014 alone. In addition, the potential risks of contaminating potable water aquifers (e.g., leakage of disposal wells and geological connectivity) and inducing seismicity and earthquakes are high. As such, disposal wells may be limited or not available for producers in some states (e.g., Pennsylvania). The alternative of a long distance hauling and disposing of PW in deep wells in neighboring states is also relatively expensive. For example, the combined cost of trucking PW from Pennsylvania to a neighboring state and disposing PW in deep wells in the neighboring state may be $10-15 per barrel.

The staggering volume of PW indicates the least the dependency of hydro-fracturing on potable water, if not overuse or depletion of potable water resources, where hydro-fracturing may compete with other uses especially in water distressed areas. Yet, direct disposal of PW in deep wells is becoming not easily accessible, relatively expensive and very risky. Yet, the predominant theme so far in treating PW is dilution, but dilution is not a solution to pollution. Pseudo treatment of PW, especially when the content of PW, whether it's in a liquid or a solid form, is released into groundwater, surface water, domestic wastewater treatment plants, public roads (e.g., via roads de-icing salts) and landfills, spreads contaminants wider and further even if the release is within regulations. Such critical issues open the door for promoting and developing innovative methods to properly treat and reuse PW.

THE OBJECTIVES OF THE INVENTION

No more logical approach would seem to present itself than treating PW by simple and economical de-salting methods after effective de-scaling (selective removal of toxic, radioactive and scaling species) and de-oiling. As such, the objectives of this invention are to provide inventive methods to effectively treat PW.

SUMMARY OF THE INVENTION

In one aspect, the present invention provides a method for treating PW. The inventive method comprising the steps of: (a) separating magnesium, calcium, strontium, barium and radium from PW to produce de-scaled PW; and (b) recovering at least a portion of an amine solvent from de-scaled PW by a stripping unit to produce treated PW. Magnesium, calcium, strontium, barium and radium are separated from PW in step (a) by: (i) mixing PW with the amine solvent and humic acid to form precipitates comprising magnesium, calcium, strontium, barium and radium hydroxides, and foulants and in a precipitator unit; and (ii) removing the precipitates by a filter to produce de-scaled PW.

In another aspect, the present invention provides a method to treat PW. The inventive method comprises the steps of: (a) separating barium and radium from PW to produce first de-scaled PW; (b) separating magnesium from first de-scaled PW to produce second de-scaled PW; (c) separating strontium from second de-scaled PW to produce third de-scaled PW; and (d) recovering at least a portion of an amine solvent from third de-scaled PW by a stripping unit to produce treated PW. Barium and radium are separated from PW in step (a) by: (i) mixing PW with the amine solvent and a sulfate source to form first precipitates comprising barium and radium sulfates in a first precipitator unit; and (ii) removing the first precipitates by a first filter to produce first de-scaled PW. Magnesium is separated from first de-scaled PW in step (b): by (i) mixing first de-scaled PW with the amine solvent to form second precipitates comprising magnesium hydroxide in a second precipitator unit; and (ii) removing the second precipitates by a second filter to produce second de-scaled PW. Strontium is separated from second de-scaled PW in step (c) by: (i) mixing second de-scaled PW with humic acid to form third precipitates comprising strontium hydroxide in a third precipitator unit; and (ii) removing the third precipitates by a third filter to produce third de-scaled PW.

In yet another aspect, the present invention provides a method to treat PW. The inventive method comprises the steps of: (a) separating barium and radium from PW to produce first de-scaled PW; (b) separating magnesium from first de-scaled PW to produce second de-scaled PW; (c) separating strontium from second de-scaled PW to produce third de-scaled PW; and (d) recovering at least a portion of an amine solvent from third de-scaled PW by a stripping unit to produce treated PW. Barium and radium are separated from PW in step (a) by: (i) mixing PW with the amine solvent to form first precipitates comprising barium and radium sulfates in a first precipitator unit; and (ii) removing the first precipitates by a first filter to produce first de-scaled PW. Magnesium is separated from first de-scaled PW in step (b) by: (i) mixing first de-scaled PW with the amine solvent to form second precipitates comprising magnesium hydroxide in a second precipitator unit; and (ii) removing the second precipitates by a second filter to produce second de-scaled PW. Strontium is separated from second de-scaled PW in step (c) by: (i) mixing second de-scaled PW water with humic acid to form third precipitates comprising strontium hydroxide in a third precipitator unit; and (ii) removing the third precipitates by a third filter to produce third de-scaled produced.

In yet another aspect, the present invention provides a method to treat PW. The inventive method comprises the steps of: (a) separating barium and radium from PW to produce first de-scaled PW; (b) separating magnesium and strontium from first de-scaled PW to produce second de-scaled PW; (c) separating sulfate from second de-scaled PW to produce third de-scaled PW; and (d) recovering at least a portion of an amine solvent from third de-scaled PW by a stripping unit to produce treated PW. Barium and radium are separated from PW in step (a) by: (i) mixing PW with the amine solvent to form first precipitates comprising barium and radium sulfates in a first precipitator unit; and (ii) removing the first precipitates by a first filter to produce first de-scaled PW. Magnesium and strontium are separated from first de-scaled PW in step (b) by: (i) mixing first de-scaled PW with the amine solvent and humic acid to form second precipitates comprising magnesium and strontium hydroxides in a second precipitator unit; and (ii) removing the second precipitates by a second filter to produce second de-scaled PW. Sulfate is separated from second de-scaled PW in step (c) by: (i) mixing second de-scaled PW water with the amine solvent, and either aluminum hydroxide or iron hydroxide to form third precipitates comprising either calcium sulfoaluminate or calcium sulfoferrate in a third precipitator unit; and (ii) removing the third precipitates by a third filter to produce third de-scaled PW.

In yet another aspect, the present invention provides a method to treat PW. The inventive method comprises the steps of: (a) separating barium, radium, magnesium and strontium from PW to produce first de-scaled PW; (b) separating sulfate from first de-scaled PW to produce second de-scaled PW; and (c) recovering at least a portion of an amine solvent from second de-scaled PW by a stripping unit to produce treated PW. Barium, radium, magnesium and strontium are separated from PW in step (a) by: (i) mixing PW with the amine solvent and humic acid to form first precipitates comprising barium and radium sulfates, and magnesium and strontium hydroxides in a first precipitator unit; and (ii) removing the first precipitates by a first filter to produce first de-scaled PW. Sulfate is separated from first de-scaled PW in step (b) by: (i) mixing first de-scaled PW water with the amine solvent, and either aluminum hydroxide or iron hydroxide to form second precipitates comprising either calcium sulfoaluminate or calcium sulfoferrate in a second precipitator unit; and (ii) removing the second precipitates by a second filter to produce second de-scaled PW.

Prior to conducting the above described inventive methods ([0010] to [0014]), PW further comprises the step of simultaneously de-oiling PW and de-watering oil by hydrophobic membranes.

Treated PW resulting from the above described inventive methods ([0010] to [0014]) further comprises the step of de-salting by a desalination train, wherein the desalination train comprises at least a heat exchanger, a plurality of flashing stages arranged in series and at least a compression device, feeding treated PW to be desalinated through the heat exchanger and then in succession through the flashing stages to bring treated PW to a vaporizing temperature by maintaining the flashing stages at progressively lower pressures in the direction of going down the flashing stages, thereby treated PW at saturation temperature corresponding to the pressure in a flashing stage flows to a next succeeding flashing stage at a lower pressure and arrives in the next flashing stage at a temperature higher than the saturation temperature corresponding to the lower pressure in the next flashing stage so that at least a portion of treated PW flashes into vapor in each of the flashing stages, withdrawing vapor from each of the flashing stages, compressing at least a portion of the withdrawn vapor by the compression device, condensing the compressed vapor in the heat exchanger thereby producing distillate and heating treated PW before entering a first flashing stage of the desalination train, and withdrawing unflashed treated PW from a last flashing stage of the desalination train as reject brine. The flashing stages comprise hydrophobic membranes under reduced pressure. The flashing stages further comprise vapor-liquid separators under reduced pressure, wherein the vapor-liquid separators comprise hydrophobic demister pads. The compression device is driven mechanically, thermally, and combinations thereof. Reject brine further comprises the step of recycling at least a portion of reject brine for mixing with treated PW prior to entering the heat exchanger.

The above described desalination train ([0016]) further comprises interrelating it in a brine-forward desalination system, wherein the brine-forward desalination system comprises a plurality of the desalination train arranged in series, in which each desalination train comprises at least the heat exchanger, the plurality of flashing stages arranged in series and at least the compression device, each of the desalination train produces distillate and reject brine, reject brine from each desalination train except a last desalination train in the brine-forward desalination system passes through to feed a next succeeding desalination train, thereby each desalination train progressively possesses a higher level of total dissolved solids (TDS) than a preceding desalination train, and reject brine from the last desalination train in the brine-forward desalination system is rejected at a level not exceeding 250,000 mg/L of TDS, thereby the brine forward desalination system is a multi-flashing system without supplying additional heat after the heat exchanger of each desalination train, and a multi-concentration system without supplying additional treated PW after a first heat exchanger of a first desalination train.

Yet, treated PW resulting from the above described inventive methods ([0010] to [0014]) further comprises the step of de-salting by a desalination train, wherein the desalination train comprises at least a heat exchanger, a plurality of flashing stages arranged in parallel and at least a compression device, feeding treated PW to be desalinated through the heat exchanger and then in parallel through the flashing stages to bring treated PW to a vaporizing temperature by maintaining the flashing stages at a lower pressure, treated PW at saturation temperature corresponding to the low pressure in the flashing stages or at a temperature higher than the saturation temperature corresponding to the lower pressure in the flashing stages so that at least a portion of treated PW flashes into vapor in each of the flashing stages, withdrawing vapor from each of the flashing stages, compressing at least a portion of the withdrawn vapor by the compression device, condensing the compressed vapor in the heat exchanger thereby producing distillate and heating treated PW before entering each of the flashing stages, and withdrawing unflashed treated PW from each of the flashing stages as reject brine of the desalination train.

Yet, the above described desalination train ([0018]) further comprises interrelating it in a brine-forward desalination system, wherein the brine-forward desalination system comprises a plurality of the desalination train arranged in series, in which each desalination train comprises at least the heat exchanger, the plurality of flashing stages arranged in parallel and at least the compression device, each of the desalination train produces distillate and reject brine, reject brine from each desalination train except a last desalination train in the brine-forward desalination system passes through to feed a next succeeding desalination train, thereby each desalination train progressively possesses a higher level of total dissolved solids (TDS) than a preceding desalination train, and reject brine from the last desalination train in the brine-forward desalination system is rejected at a level not exceeding 250,000 mg/L of TDS, thereby the brine forward desalination system is a multi-flashing system without supplying additional heat after the heat exchanger of each desalination train, and a multi-concentration system without supplying additional treated PW after a first heat exchanger of a first desalination train.

This invention is of particular interest in connection with applications such as, but is not limited to, unconventional oil and gas production, conventional oil and gas production, mine drainage water, flue gas desulfurization wastewater, agricultural drainage water, road de-icing salt production, sodium carbonate production, saline water desalination, mining, geothermal power plants, treatment of contaminated water sources (e.g., surface water or ground water) by produced water, natural brine or drainage resulting from all kinds of mining operations, and other related or similar applications.

This invention is not restricted to use in connection with one particular application. Further objects, novel features, and advantages of the present invention will be apparent to those skilled in the art upon examining the accompanying drawings and upon reading the following description of the preferred embodiments, or may be learned by practice of the invention.

The above mentioned figures, being merely exemplary, contain various elements that may be present or omitted from actual process implementations depending upon the circumstances. The figures are drawn in a way that illustrates at least those elements that are significant for an understanding of the various embodiments and aspects of the invention. However, various other elements of the unique inventive methods, and the combination of apparatus for carrying out the methods, are also shown and/or briefly described to understand how various features, including optional or alternate features, may be utilized to provide an efficient and low cost design that can be conducted in a desired configuration, throughput size, and optimum operation.

DESCRIPTION OF THE PREFERRED EMBODIMENT

De-Salting by Hydrophobic Membranes

Figure 1:
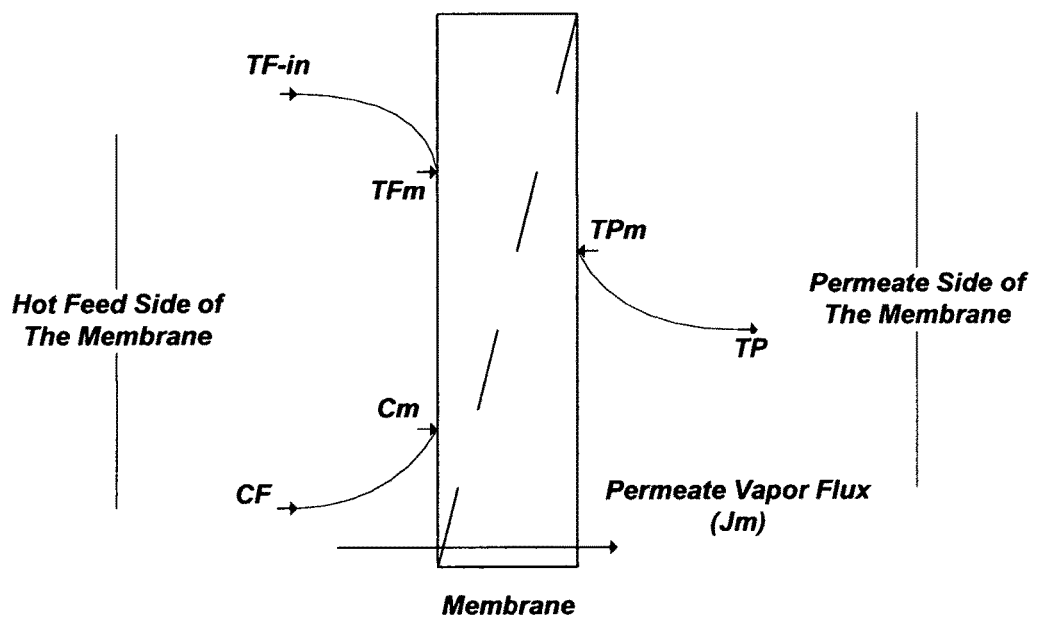
FIG. 1 illustrates concentration and temperature polarization profiles in hydrophobic membranes as a de-salting method.

Membrane Distillation (MD), for instance, refers to the transport of the vapor phase through pores of a hydrophobic membrane that separates two liquid solutions [e.g., U.S. Pat. Nos. 6,365,051; 6,663,778; 7,093,663; 7,392,848; 7,501,065; 7,789,159; 7,963,338; and 8,915,301]. The liquid solutions cannot enter the membrane's pores unless the applied pressure is greater than the specified "capillary or liquid entry" pressure for the porous partition of the membrane. In the absence of such a pressure, vapor-liquid interfaces are formed on both sides of the membrane's pores due to surface tension forces. Under these conditions, if a temperature difference is applied, a vapor pressure gradient will be created on both interfaces. Evaporation will take place at the hot membrane interface (feed), water vapor will transport through the membrane's pores with a convective and/or diffusion mechanism, and vapor condensation will take place at the cold side of the membrane interface (permeate). Thus, the net permeate vapor flux will be from the hot feed stream to the cold condensate stream. FIG. 1 shows a simplified schematic diagram for the flow direction in MD.

MD has several clear advantages compared to conventional pressure-driven hydrophilic membranes (e.g., RO and NF) or thermal-driven (e.g., MSF, MED, MVR and the like) de-salting methods. First, MD can take place at a very low pressure that may range from sub-atmospheric pressure to slightly above atmospheric pressure (e.g., 1.03 bar). This is contrary to RO that ought to be operated at high pressures (e.g., 60-80 bar) to exceed the natural osmotic pressure of source water such as seawater (e.g., the osmotic pressure of normal seawater is about 30 bar), which require a significant pumping power in contrast to MD. As such, RO is inapplicable to source water such as PW (e.g., Tables 1 and 2) where the level of TDS exceeds 45,000-50,000 mg/L due to osmotic pressures that cannot be overcome, which is also in contrast to MD.

Second, MD may be conducted at temperatures that are significantly lower than the normal boiling point of water. Any form of waste heat (e.g., existing low temperature gradients typically available in processing plants, hot oilfields produced water) or low grade energy sources (e.g., wind, solar, geothermal, solar ponds and combinations) may be used.

Third, the MD permeate stream (distillate) from any source water containing non-volatile ions is an ultra-pure. Entrainment of dissolved ions in the permeate stream, which is an issue with RO and NF membranes, is thus negligible.

Fourth, the evaporation surface of MD can be configured similar to the available various pressure-driven hydrophilic membranes (e.g., hollow fiber, spiral wound and flat sheet configurations). The modularity of MD thus allows the ease of adding processing capacity as needed. The natures of bulky conventional thermal-driven processes (e.g., MSF, MED, MVR and the like) prohibit furnishing the flexibility and simplicity that MD provides.

However, the apparent simplicity of MD obscures complex and simultaneous mass and heat transfer interactions. The mass water vapor flux in MD is a function of the "membrane permeability coefficient" ($K_m$) and the vapor pressure difference across the membrane:

$$J_m = K_m[p_{Fm}^s(T_{Fm}) - p_P] \quad (1)$$

where $p_{Fm}^s$ is the saturated vapor pressure of the hot feed stream at the membrane surface temperature ($T_{Fm}$) rather than the bulk (inlet) feed temperature ($T_F$), and $p_P$ is the permeate stream pressure. $K_m$ is a function of the membrane structure such as porosity ($\varepsilon$), pore size radius (r), thickness ($\delta$), and tortuosity ($\chi$):

$$K_m = \frac{2\varepsilon r}{3\chi\delta} \frac{1}{RT} \sqrt{\frac{8\,RT}{\pi}} \quad (2)$$

$T_{Fm}$ as the driving force for the water vapor flux across the membrane, not only affects the vapor-liquid equilibrium in the feed stream but also affects the hydrodynamics in the feed stream liquid phase since its dependent on salts concentrations at the membrane surface.

As evaporation in MD takes place, the viscosity of a saline feed stream increases with increasing salts concentrations. This would elevate the osmotic pressure, depress the vapor pressure, and alter heat and mass transfer coefficients across the membrane boundary layers. The saturated vapor pressure of a saline stream can be related to its osmotic pressure as follows:

$$p_{Fm}^s = \frac{p^o}{\exp\left[\frac{\Pi_{Fm} \tilde{v}_w}{RT_{Fm}}\right]} \quad (3)$$

where at $T_{Fm}$, $p_{Fm}^s$ is the saturated vapor pressure of a saline stream (mmHg), $p^o$ is the vapor pressure of pure water (mmHg), $\Pi_{Fm}$ is the osmotic pressure of a saline stream (psi), $\tilde{v}_w$ is the water molar volume (L/gmol), and R is the ideal gas constant (L psi/gmol K).

$p^o$ can be accurately estimated using Antoine equation. The osmotic pressure ($\Pi_{Fm}$) of a saline stream can be estimated as follows:

$$\Pi = 1.19 T_{Fm} \Sigma M_i \quad (4)$$

where $M_i$ is the molar concentration of individual ions (mol/L).

Eqs. (1) to (3) imply that in order to enhance or achieve an acceptable level of the vapor flux, the value of either $K_m$, or $T_{Fm}$, or both values must be increased. As given in Eq. (2), the membrane structure is the key to optimize $K_m$. The $K_m$ value of hydrophobic membranes is typically very low (e.g., about 0.2 Kg/m$^2$·hr·mmHg) to prevent water (liquid) from passing through the membrane's pores. A slight increase in the $K_m$ value is possible, which could drastically improve vapor flux, but it should not be at the expense of losing the membrane hydrophobicity. As such, a balance ought to be stricken between improving the value of $K_m$ and maintaining the hydrophobicity of the membrane.

$K_m$ is also, to some degree, temperature dependent (decreases by 3% with a 10° C. increase in the mean temperature). The molecular mean free path for water vapor at 60° C. is about 0.3 µm. If convective transport is dominant across the membrane, the controlling factor will be the size of the membrane's pores. If diffusive transport is dominant; however, the controlling factor will be the average mole fraction of air present within the membrane's pores. Using an inappropriate small size of membrane's pores combined with an increase in the feed stream temperature range (e.g., above 60° C.) could subsequently lead to an unintended reduction in $K_m$.

The key to increasing the value $T_{Fm}$ lies within: (1) the thermal conductivity of the hydrophobic membrane and the nature of the condensation method on the permeate side of the membrane; (2) the thermal stability of the hydrophobic membrane, the characteristics of the flow regime, and the operating conditions (e.g., the feed stream's temperature and flow rate, and the permeate stream's pressure); and (3)

controlling scaling compounds in (if not removing scaling compounds from) the feed stream.

The Permeate Water Vapor Condensation Method

The thermal mechanism in the MD hot feed stream takes place in two forms. The first form is the latent heat, which is utilized to evaporate water at the feed side (hot) of the membrane interface. The second form is the conductive heat, which is lost in transferring water vapor through the membrane layer to the permeate side (cold) of the membrane interface. For effective MD, the extent of the conductive heat loss must be minimized.

Figure 2:
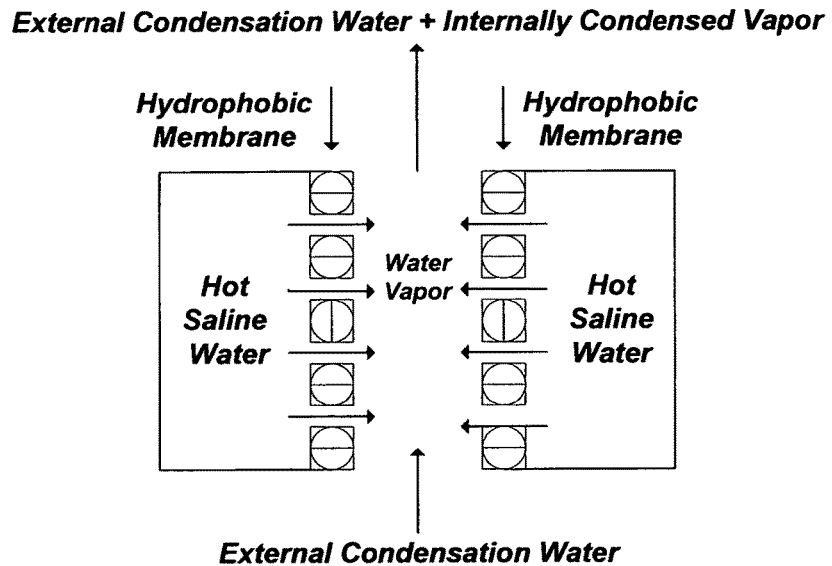
FIG. 2 illustrates an internal vapor condensation (Configuration A) and an external vapor condensation (Configuration B) of de-salting by hydrophobic membranes.
Figure 2:
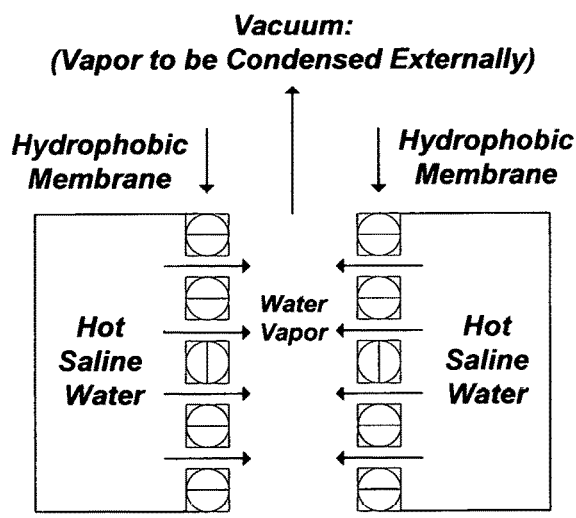

The permeate vapor condensation step can be accomplished internally (within the membrane module) or externally outside the membrane module. As shown in FIG. 2 (Configuration A), one of the methods to conduct the internal condensation is by directly contacting, for example, a water (e.g., potable) stream at ambient temperature along the permeate surface of the hydrophobic membrane to condense vapor. Since the vapor pressure of the water stream at the condensation-membrane interface (e.g., the cold side of the membrane) is much lower than the vapor pressure of the hot water feed stream steam at the evaporation-membrane interface, vapor is transferred from the hot stream through the membrane's pores to the flowing cold water stream. However, the extent of the conductive heat loss in this "Direct Contact Membrane distillation" (DCMD) method is considerable.

As shown in FIG. 2 (Configuration B); however, an external condensation method can be achieved under reduced pressure (vacuum) to withdraw vapor from the hot-side of the membrane interface and condense it in an external condenser outside the membrane module. In this "Vacuum Membrane Distillation (VMD) method, and when vapor-liquid equilibrium is favorable, the potential for drastically achieving higher vapor flux and substantially minimizing the extent of conductive heat loss from the hot feed stream is attainable.

Operating Conditions

One of the major advantages of VMD (FIG. 2; Configuration B) relative to DCMD (FIG. 2; Configuration A) is that the conductive heat transfer across the membrane layer is nearly negligible. This is attributed to the applied vacuum that allows a very low gas pressure on the permeate side of the membrane and prevents the presence of trapped air in the membrane's pores (e.g., reduces resistance to vapor flow). As such, the heat flux ($J_h$) at the hot feed stream side of the membrane interface can be expressed as follows:

$$J_h = K_h[T_{F-in} - T_{Fm}] \quad (5)$$

where $K_h$ is the "membrane heat transfer coefficient" that can be estimated from the Nusselt number, and $T_{F-in}$ is the inlet hot feed stream temperature entering the membrane module. Since the value of $T_{Fm}$ cannot practically be determined, $J_h$ can be related to the practically measurable temperature drop between the inlet and outlet of the hot feed stream through the membrane module as follows:

$$J_h = \frac{Q_F}{A_m} c_p [T_{F-in} - T_{F-out}] \quad (6)$$

where $Q_F$ is the hot feed stream flow rate, $A_m$ is the total membrane area, $c_p$ is the liquid phase heat capacity, and $T_{F-out}$ is the feed stream temperature leaving the membrane module. Knowing the value of $J_h$ from Eq. (6) along with roughly estimating the value of $K_h$ from an appropriate Nusselt number, the hot feed stream at the membrane surface temperature ($T_{Fm}$), which is responsible for the temperature polarization phenomenon, can be predicted.

The heat flux is related to the mass vapor flux as follows:

$$J_h = J_m \Delta H_v \quad (7)$$

where $\Delta H_v$ is the water heat of vaporization. For a laminar flow, it is fundamentally known that $K_h$ in a cross flow configuration (e.g., a saline stream flows in the shell side of the hollow fiber module and vacuum in the tube side) is much higher than its correspondent value in a parallel flow configuration (e.g., a saline stream flows in the tube side of the hollow fiber module and vacuum in the shell side). Thus, the cross flow configuration in MD is essential to achieve higher permeate vapor flux.

According to Eq. (6), the flow rate and temperature in the feed stream have appreciable effects on the permeate vapor flux. At a given inlet feed stream temperature, increasing the feed stream flow rate would increase both $K_h$ and $T_{Fm}$. Another benefit for applying a higher feed flow rate is reducing the residence time of the hot feed stream passing through the membrane module, thereby appreciably minimizing the temperature drop in the outlet feed stream. This is critical for thermal efficiency, especially in staging properly configured hydrophobic membranes (e.g., VMD) as a de-salting method.

De-Oiling/De-Watering by Hydrophobic Membranes

An oil-water stream, depending on it is water cut and viscosity, may be a "water-in-oil" (W/O) stream (may also refer to as a W/O emulsion) or an "oil-in-water" (O/W) stream (may also refer to as an O/W emulsion). The water cut in an oil-water stream is the ratio of the water volume to the volume of total produced liquids (water and oil). A W/O stream means oil is the "primary" (e.g., continuous) phase while water is the "secondary" (e.g., dispersed) phase. On the other hand, an O/W stream means water is the "primary" (e.g., continuous) phase while oil is the "secondary" (e.g., dispersed) phase.

Figure 3:
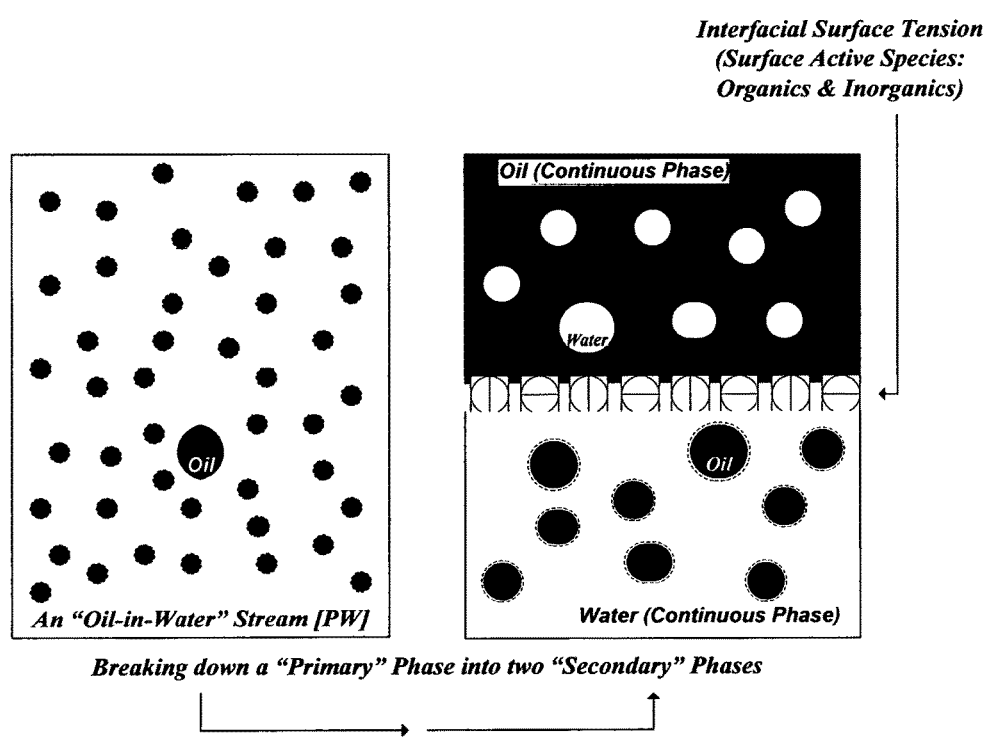
FIG. 3 illustrates the breakdown of a primary emulsion (e.g., PW) into two secondary emulsions.

Conventional oil-water separation methods are generally inefficient, whether the stream is an O/W (e.g., PW) or a W/O (e.g., wet oil), since they basically break down a given "primary" phase into two "secondary" phases; one is richer and the other one is poorer in the "secondary" phase of the "primary" phase. FIG. 3 illustrates such conventional oil-water separation methods. Here, the illustrated oil-water stream is O/W (e.g., PW), wherein the "primary" phase is water. When the "primary" phase is broken down into two "secondary" phases (by, for example, a gravity separator such as a skim tank), an accelerated separator such as a hydrocyclone or a centrifuge, or a combination), neither the water phase is sufficiently de-oiled (e.g., does not meet PW regulations) nor is the oil phase sufficiently de-watered (e.g., does not meet oil specifications). As such, each of the phases (oil and water) requires further multiple and intricate processing steps. Yet, charged organic species (e.g., oxygen-, nitrogen-, and sulfur-containing species) often exist in PW, which not only hinder the segregation of the oil phase from the water phase but also contribute to scale formation in the water phase.

However, water de-oiling and oil de-watering are synonymous. Therefore, they should be simultaneously targeted by an efficient method. Here, "de-oiling" refers to the separation of the Total Oil Content (TOC) from water, which comprises the sum of dispersed oil and dissolved oil in water. "De-watering" refers to the separation of the water content from oil, which comprises dissolved salts within the water content in oil.

The natural demulsification of oil-water starts in downhole wherein oil may preferentially squeeze through the narrow pores of organically surface coated rocks (e.g., oil wet sandstone, limestone, dolomite, and combinations thereof) and trapped by impermeable rocks (e.g., clay or shale). In such a natural downhole capillary flow, no shear, no differential velocity (velocity is in the direction of the flow) or oil droplets rotation are induced. Thus, the capillary flow, especially with low capillary forces, is the most efficient method to separate oil from water.

Figure 4:
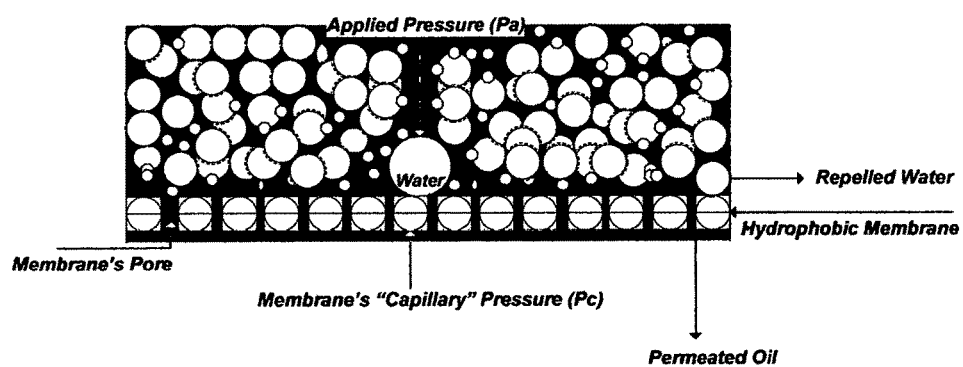
FIG. 4 illustrates the water de-oiling and oil de-watering concept by hydrophobic membranes.

My de-oiling/de-watering concept [U.S. Pat. No. 6,365,051 (filed on Oct. 12, 1999); U.S. Pat. No. 7,789,159 (filed on Jun. 28, 2008); U.S. Pat. No. 7,934,551 (filed on Feb. 7, 2009); U.S. Pat. No. 7,963,338 (filed on Feb. 27, 2009); and U.S. Pat. No. 8,915,301 (filed on Apr. 26, 2011)] is analogous to the natural demulsification phenomenon of oil in downhole reservoirs. The inventive concept is illustrated in FIG. 4, whether water is the continuous phase (an O/W stream such as PW) or water is the dispersed phase (a W/O stream such as certain wet oil). Here, by utilizing the hydrophobic interactions between oil and water (essentially immiscible fluids) along with a properly configured hydrophobic membrane, water (the membrane's non-wetting fluid) would be efficiently repelled while oil (the membrane's wetting fluid) would be permeated through the hydrophobic membrane by applying a low pressure.

Hydrophobic interactions are thermodynamic phase and energy related phenomena. The energy of interactions between water and hydrophobic molecules can be expressed thermodynamically by the Gibbs free energy as follows:

$$\Delta G = \Delta H - T\Delta S \tag{8}$$

where $\Delta G$ is the free energy of between water and hydrophobic molecules, $\Delta H$ is the enthalpy that represents the mixing degree between water and hydrophobic molecules, T is the temperature, and $\Delta S$ is the entropy that represents the mixing disorder between water and hydrophobic molecules.

The mixing degree of water and hydrophobic molecules depends largely on the enthalpy, which may be re-expressed as follows:

$$\Delta H = 2\Delta H_{w-h} - \Delta H_{w-w} - \Delta H_{h-h} \tag{9}$$

where "w" is a water molecule and "h" is a hydrophobic molecule. Water and hydrophobic molecules would not mix if the water molecule and hydrophobic molecule made more favorable interactions with themselves ("w-w" and "h-h") than they would make with one another ("w-h"). On the other hand, Eq. (8) implies that the mixing tendency would increase with temperature but the mixing tendency is governed by the entropy (the disordering property).

There may be three main oil-water interactions: (1) ion hydration between charged organic groups (e.g., oxygen-, nitrogen-, and sulfur-containing species); (2) hydrogen bonding between polar organic groups and water; and (3) hydrophobic hydration (e.g., neutral organic groups). In the absence of a hydrophobic molecule, the geometry of a polar water molecule in a pure aqueous phase is tetrahedron wherein the center of the water molecule is positioned in 6 possible hydrogen bonding configurations. When a water molecule in an aqueous phase is replaced by a neutral hydrophobic molecule that may not form a hydrogen bond, one of the edges of the tetrahedron water molecule collapses, thereby reducing the number of possible hydrogen bonding configurations to 3 (instead of 6). In hydrophobic hydration, the configurational freedom of water molecules is reduced in the proximity of apolar residues (e.g., neutral organic species). This ordering of water molecules results in a loss of entropy (e.g., reduces the entropy of the central water molecule by 50%).

In contrast to pure water; however, PW is a saline stream and its salts content may be extreme (e.g., Tables 1 and 2). This results in an increase in the surface tension of PW, which, in turn, increases hydrophobic interactions between oil and water. Oil responds to this situation by decreasing its surface area in an attempt to minimize contact with water, which is manifested by folding (the folded conformation is more compact than the unfolded one) and then self-association. As such, the entropy may be expressed as follows:

$$\Delta S = S_w - S_h \tag{10}$$

where $S_w$ is the entropy in the water phase, and $S_h$ is the entropy on the hydrophobic surface interface. Eq. (10) implies that both folding and self-association of oil free up bound water, increase the entropy (favors de-mixing), and thus reduce the Gibbs free energy (Eq. (8)). As such, hydrophobic interactions are a thermodynamic-driven process that seeks to minimize the free energy by minimizing mixing between water and hydrophobic molecules.

Hydrophobic membranes are not based on size-exclusion such as hydrophilic filtration membranes (e.g., microfiltration and ultrafiltration), wherein such hydrophilic membranes allow water to pass through and reject species based on their sizes. Such hydrophilic membranes also result in breaking down a given "primary" phase into two "secondary" phases; one is richer and the other one is poorer in the "secondary" phase of the "primary" phase (FIG. 3). Here again, their permeate streams (water) are insufficiently de-oiled, and their reject streams are largely oily waste streams. In contrast, hydrophobic membranes do not permit passage of water through the membrane until the water capillary pressure ($p_c$) of the hydrophobic membrane is exceeded. $p_c$ depends on the interfacial tension, contact angle, and the pore size distribution of the hydrophobic membrane as reflected by the following relation:

$$p_c = \frac{2\tau_{w-o}\cos\theta_{w-o}}{r} \tag{11}$$

where $\tau_{w-o}$ is the water-oil interfacial tension, $\theta_{w-o}$ is the contact angle of a water droplet on the membrane surface in the presence of oil, r is the radius of the membrane's pore. The value of the $\theta_{w-o}$ can be related to various interfacial tensions as follows:

$$\cos\theta_{w-o} = \frac{\tau_{m-w} - \tau_{m-o}}{\tau_{w-o}} \tag{12}$$

where $\tau_{m-w}$ is interfacial tension of a membrane in contact with water, and $\tau_{m-o}$ is the interfacial tension of the membrane in contact with oil. When $\tau_{m-w}$ is greater than $\tau_{m-o}$, the membrane is hydrophobic ($0<\theta_{w-o}<90°$), which means that the value of $p_c$ is positive and thus the membrane is oil wet that permits the passage of oil and repels water. However, when $\tau_{m-w}$ is lower than $\tau_{m-o}$, the membrane is hydrophilic ($\theta_{w-o}>90°$). This means that the value of $p_c$ is negative, and the membrane is water wet that permits the passage of water and prevents oil from entering the membrane pores against the applied pressure (pa).

De-Scaling by Precipitation

The Liquid-Phase Precipitation (LPP) process is based on mixing an aqueous stream with a suitable solvent at ambient temperature and atmospheric pressure to form selective ionic precipitates. The suitable solvents are those which have the capability to meet two basic criteria.

The first criteria is the suitability to precipitate targeted ionic species (charged inorganics and organics) from aqueous solutions. The selected organic solvent must be miscible with the aqueous phase. Of equal importance, the targeted ionic species must be sparingly soluble in the organic solvent. The addition of such a solvent to an ionic-aqueous solution leads to the capture of part of the water molecules and reduces the solubility of ionic species in the water which form insoluble precipitates. The solubility of the targeted ionic species in the organic solvent is a critical factor in achieving the degree of saturation. Therefore, solubility related factors such as ionic charge, ionic radius, and the presence of a suitable anion in the aqueous solution play an important role in affecting and characterizing precipitates formation.

The second criteria is suitability for overall process design. For ease of recovery, the selected solvent must have favorable physical properties such as low boiling point, high vapor pressure, high relative volatility, and no azeotrope formation with water. From a process design standpoint, the selected solvent must have low toxicity since traces of the organic solvent always remain in the discharge stream. Further, the selected solvent must be chemically stable, compatible, and relatively inexpensive.

Several organic solvents have been identified for potential use in the LPP process. These solvents are isopropylamine (IPA), ethylamine (EA), propylamine (PA), dipropylamine (DPA), diisopropylamine (DIPA), diethylamine (DEA), and dimethylamine (DMA). However, IPA is the preferred solvent in the LPP process. The preference of IPA is attributed to its high precipitation ability with different ionic species, favorable properties (boiling point: 32.4° C.; vapor pressure: 0.64 bar 20° C.); and low environmental risks.

Nitrogen ($N_2$) can form compounds with only three covalent bonds to other atoms. An ammonia molecule contains $sp^3$-hybridized nitrogen atom bonded to three hydrogen atoms. An amine molecule contains $sp^3$-hybridized nitrogen atom bonded to one or more carbon atoms. The nitrogen has one orbital filled with a pair of unshared valence electrons, which allows these solvents to act as bases. Thus, the organic solvents (ammonia and amines) are weak bases that could undergo reversible reactions with water or acids. However, when such solvents react with an acid, the unshared electrons of the solvent are used to form sigma bond with the acid, which would transform the solvent into an anionated (acidified) form. Such solvents in anionated forms act as weak acids. Acids that are found useful in this invention to generate such solvents in anionated forms comprise sulfuric acid, hydrochloric acid, perchloric acid, hypochlorous acid, nitric acid, citric acid, sulfuric acid, sulfonic acid, phosphoric acid, formic acid, acetic acid, propionic acid, butyric acid, pentanoic acid, hexanoic acid, pyruvic acid, lactic acid, caproic acid, oxalic acid, malonic acid, succinic acid, glutaric acid, adipic acid, humic acid, fulvic acid, and combinations thereof. Such solvents can be regenerated from their anionated forms by a hydroxide source (an inorganic source, an organic source, and combinations thereof).

Improving the performance of LPP is always a target. One of the essential improvements is to minimize, if not eliminate, the use of the organic solvent. Inorganic additives can alternatively replace organic solvents or can be used in addition to organic solvents to induce precipitation of targeted species. The suitable inorganic additives for LPP are those that can form an insoluble inorganic-based compound of targeted charged species in an aqueous stream. Such inorganic additives should preferably be recoverable and recyclable, useable as a useful by-product, or produced locally from reject or waste streams. Also, such inorganic additives should not, themselves, constitute pollutants. Several inorganic additives were indentified, developed, and tested for LPP.

A second targeted improvement for LPP is to produce controllable precipitates that are uniformly distributed with high yield and preferably in submicron sizes. Submicron precipitates are fundamentally stable and form spontaneously if a narrow resistance time distribution is improvised and/or a surface active agent (naturally existing or induced) sufficiently acts as a dispersant to prevent immediate agglomeration of the newly formed precipitates. Submicron precipitates are thus dispersed phase with extreme fluxionality. On the other hand, non-spontaneous unstable macro-size precipitates will form if given sufficient time to rest.

The state (stabile, metastabe, or unstable) of given precipitates can be expressed thermodynamically by the Gibbs free energy relation as given in Eq. (8). Here in Eq. (8), $\Delta G$ is the free energy of precipitates, $\Delta H$ is the enthalpy that represents the binding energy of the dispersed phase precipitates in water, and $\Delta S$ is the entropy of the dispersed phase precipitates (the state of precipitates disorder). The binding energy ($\Delta H$) can be expressed in terms of the surface tension (r) and the increase in the surface area ($\Delta A$) as follows:

$$\Delta G = r \Delta A - T \Delta S \qquad (13)$$

When the introduced free energy into the aqueous stream exceeds the binding energy of precipitates, individual precipitates are broken down and redistributed. In addition, when a surface active agent is present in the aqueous stream as an effective dispersant, r is reduced and thus the precipitates binding energy is diminished. Furthermore, part of the introduced energy may not contribute to precipitates' deflocculating but it dissipates in the aqueous stream in the form of heat which reduces viscosity. All of these factors increase precipitates dispersion or disorder (positive entropy). As such, the change in the entropy ($\Delta S$) quantitatively defines precipitates dispersion (solvation).

The Compressed-Phase Precipitation (CPP) process was also developed to achieve sub-micron precipitates in certain applications. CPP is conceptually similar to LPP in which the targeted ionic species must be nearly insoluble in the organic solvent whereas the mother solvent (water) is miscible with the organic solvent. However, the difference is that fluids in the CPP process can be subjected to pressure and/or temperature manipulations, or fluids modifications to force unusual thermo-physical properties (e.g., exhibit liquid-like density but with higher diffusivity, higher compressibility and lower viscosity).

The fast diffusion combined with low viscosity of a compressed organic solvent into an aqueous phase produces faster supersaturation of targeted ionic species, and their possible precipitation in the desired and sub-micron and micron sizes. Thus, the precipitate's size, size distribution, morphology, and structure can be controlled. Achieving faster supersaturation would, in turn, minimize the use of the organic solvent, reduce the size of precipitation vessels (a very short retention time), and allow the recovery of targeted ionic species in the desired precipitates shape and distribution.

Several factors could influence the performance of the precipitation process. Among such factors are: (1) the chemistry of the aqueous stream along with the identity and concentration of it is targeted species; and (2) the conditions under which precipitation is induced by mixing with additives (an inorganic additive, an organic solvent, and combinations) with the aqueous stream.

The Chemistry of PW

The Total Salt Content

PW from the Marcellus basin is essentially a chloride-type (sulfate-depleted) with appreciable median concentrations of bromide (Table 1). PW from the Barnett basin is also a chloride-type but with appreciable median concentrations of sulfate, bicarbonate and bromide (Table 2). The median TDS in Marcellus PW (157,000 mg/L) is about 3-fold higher than the median TDS in Barnett PW (51,000 mg/L). If an effective method is used to de-scale PW to render PW in the form of sodium chloride or sodium-calcium chloride, then an effective de-salting method may reject PW at a level of TDS not exceeding 250,000 mg/L (below the solubility limit of sodium chloride). An effective, simple, flexible and economical de-salting method is thus a must to beneficially reuse PW.

Sodium chloride may then be produced from reject brine of such a de-salting method, which, in turn, may be used, for example, as a: (1) road de-icing salt; (2) feedstock to produce sodium carbonate if a source of carbon dioxide is available; or (3) feedstock for chlor-alkali industries. Alternatively, sodium-calcium chloride may be produced from reject brine of a de-salting method since it is more effective for road de-icing than sodium chloride. The effectiveness of a road de-icing salt that contains an appreciable level of calcium chloride is attributed to the: (1) low freezing temperature of calcium chloride (−32° C.), which is below the freezing temperature of sodium chloride and thus more effective at colder temperatures; (2) hygroscopic nature of calcium chloride, which attracts moisture from its surroundings to jump start the ice melting action; and (3) exothermic nature of calcium chloride since as it dissolves in contact with moisture, it releases a significant amount of heat that melts ice faster than the endothermic sodium chloride and other de-icing products that must draw heat from their surroundings to dissolve and form an ice-melting brine.

The Total Scale Content

Table 1, for example, reveals that PW from the Marcellus basin has a low median concentration of bicarbonate and a very low median concentration of sulfate (essentially sulfate-depleted). However, the median concentrations of alkaline cations (except magnesium) are high. The total alkaline cations constitute about 31% of the total cations (meq./L). As a result, the total hardness (magnesium and calcium) is extremely high.

Table 2, on the other hand, shows that PW from the Barnett basin is abnormally elevated in bicarbonate and modestly richen in sulfate. The median concentrations of alkaline cations (meq./L) in Barnett's PW constitute about 13% of the total cations. However, ions pairing generally do not reach the levels of solubilities of their pure solid minerals. Only when the anion carrier is an appreciable constituent in water (e.g., sulfate in formation water), do the precipitation and dissolution (solvation) of pure phases form the dominant attenuation mechanism. Thus, the precipitation of the excess portions of the back-end alkaline cations (strontium, barium and radium) in the form of sulfates likely took place in downhole. The solvated portions of the back-end alkaline cations in the form of sulfates in PW from the Barnett basin are thus within their solubility limits. As such, the median concentrations of such alkaline cations in Barnett's PW are substantially lower than their median concentrations in Marcellus's PW. Due to the relatively high median concentration of bicarbonate, the median concentrations of magnesium and calcium are also appreciably lower in Barnett's PW than their median concentrations in Marcellus's PW. Consequently, the total hardness is much lower in Barnett's PW than that in Marcellus's PW.

Effective de-scaling of PW prior to de-salting is thus critical to: (1) isolate radioactivity, bromide, and other minor but critical species (e.g., transition metals, silica, and carbonates) from PW; (2) isolate scale-prone species and recover them as possibly useful by-products; and (3) facilitate maximizing the production of usable water and minimizing the production of reject brine by a de-salting method, thereby facilitating the production of a usable salt (e.g., sodium chloride or sodium-calcium chloride) from such reject brine. As such, de-scaling is at the heart of PW treatment and without effective de-scaling, the beneficial reuse of PW is not attainable.

The Total Oil Content

Some oil in PW may be dispersed and some of it may be dissolved. The proportions of dispersed oil and dissolved oil in PW vary considerably, and depend on the nature and the recovery method of hydrocarbons. The sum of dispersed oil and dissolved oil constitutes the Total Oil Content (TOC). In the U.S., EPA Method 1664 is the officially approved method for measuring TOC, which is defined as: "n-hexane extractable material (HEM: oil and grease) and n-hexane extractable material that is not adsorbed by silica gel (SGT-HEM: non-polar material) in surface and saline waters and industrial and domestic aqueous wastes".

Tables 1 and 2, for example, show TOC in PW from, respectively, the Marcellus and Barnett basins. Even though some of the reported TOC may seem relatively low, the removal of TOC is critical since it increases the viscosity of PW. This makes solids filtration and de-watering from PW more difficult, and interferes with the performance of de-salting methods (e.g., a foam generator, and a foulant for heat transfer surfaces and membranes).

The Inventive Methods to Treat PW

The Inventive De-Scaling Methods

Figure 5:
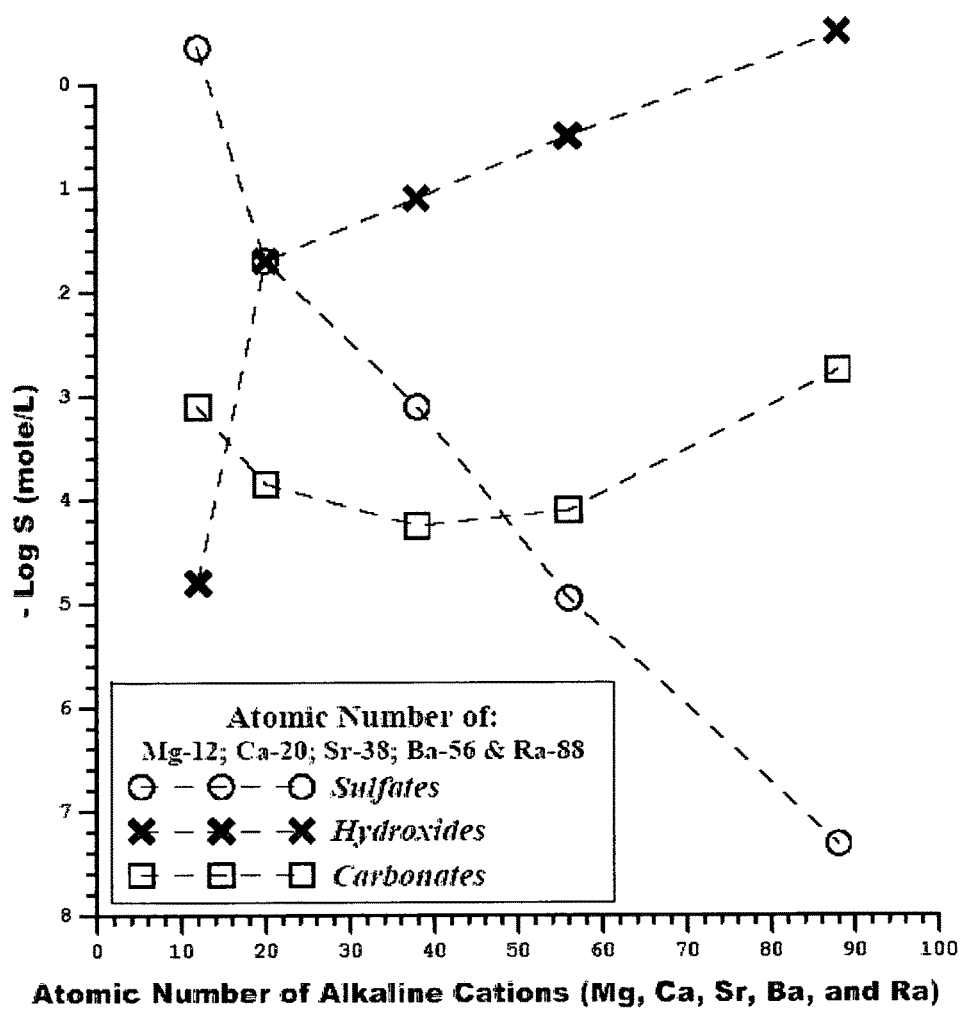
FIG. 5 illustrates the solubilities of alkaline cations in the form of sulfates, hydroxides and carbonates at 25° C.

FIG. 5 reveals that the two anions that pair with alkaline cations (magnesium, calcium, strontium, barium, and radium) with a wide range of solubilities are sulfate and hydroxide. It is clearly pronounced that solubilities of alkaline cations in the form of sulfates decrease in sequence with the increase of the atomic number (decrease of the charge density), whereas those in the form of hydroxides increase in sequence with the increase of the atomic number. Considered from a thermodynamic point of view, there is logic to such trends. This may be explained by Gibbs free energy (Eq. 8), which is the fundamental foundation for the solubility or the solubility product of a cation in a hosting anion. Enthalpy and entropy are the contributing properties to Gibbs free energy. Alkaline cations in the form of sulfates are more dependent on the relative thermodynamic properties of the cation. The enthalpies of alkaline cations are roughly equal in magnitude whereas the entropies become smaller and yet near equal as the atomic number increases, especially for barium and radium. As such, the solubilities of such alkaline cations in the form of sulfates become nearly insoluble as the atomic number increases.

The entropies of alkaline cations in the form of hydroxides, particularly of strontium, barium and radium, are much larger than those in the form of sulfates since hydroxide ions tend to disperse and lose identity when solvated. It can be inferred that Gibbs free energies of alkaline cations in the form of hydroxides are driven largely by the hosting anion (hydroxide ions) more than the relative properties of the cation. However, the front-end alkaline cations (magnesium and calcium) are much less soluble than the back-end ones (strontium, barium and radium) in the form of hydroxides. The magnitude of the enthalpy of $Mg(OH)_2$ (−114 kJ/mole) is about the same of $Ca(OH)_2$ (−130 kJ/mole) but the magnitude of the entropy (dispersion) of $Mg(OH)_2$ (−60 J/K mole) is negative and much smaller than that of $Ca(OH)_2$ (0.4 J/K mole). Thus, $Mg(OH)_2$ is much less soluble than $Ca(OH)_2$. On the other hand, the hydroxides of the back-end alkaline cations (strontium, barium and radium) are largely hydrated since they are octahydrates (Sr—Ba—Ra—$(OH)_2.8H_2O$). As a result, they are substantially more soluble than $Mg(OH)_2$ and $Ca(OH)_2$, and their solubilities appreciably increase in sequence with the increase of their atomic numbers.

FIG. 5 also shows that the solubilities of all alkaline cations in the form of carbonates are very low and fall roughly within about an order of magnitude from each other. Radium carbonate is the most soluble followed by, respectively, magnesium carbonate, calcium carbonate, barium carbonate and strontium carbonate. However, the precipitation selectivity for the less soluble alkaline cations (strontium, calcium and barium) in the form of carbonates is nearly marginal over those that are slightly more soluble (radium and magnesium). Thus, the sequential precipitation using strictly the carbonate route for the entire series of alkaline cations from PW seems inappropriate.

The most appropriate route to isolate radioactivity from PW is thus the sulfate route, which implies the co-precipitation of barium-radium sulfates. The co-precipitation of radium within the structure of barium sulfate precipitates is attributed to their near identical ionic (crystal) radius and polarizability (Table 3). Once barium and radium are precipitated in the form of sulfate from PW, the sequential precipitation of some or all of the remaining alkaline cations (magnesium, calcium and strontium) can then take place.

The hydroxide route for alkaline cations can be implemented by keeping radium and barium dissolved in PW while precipitating first the front-end alkaline cations (magnesium and calcium) sequentially or simultaneously at a basic condition. Once the front-end alkaline cations are precipitated from PW, the precipitation of barium-radium can then take place in the form of sulfates, carbonates, or any other appropriate anion pairing. Strontium, as a non-radioactive species, can be precipitated: (1) either with magnesium; or (2) in a separate precipitation stage after completing the precipitation of magnesium; or (3) with calcium; or (4) with barium-radium.

Alternatively, the hydroxide route for alkaline cations can be implemented by preferentially simultaneously binding the back-end alkaline cations (strontium, barium and radium hydroxides), preferentially selectively binding some of such back-end alkaline cations, or preferentially simultaneously binding most, if not all, alkaline cations.

Figure 6A:
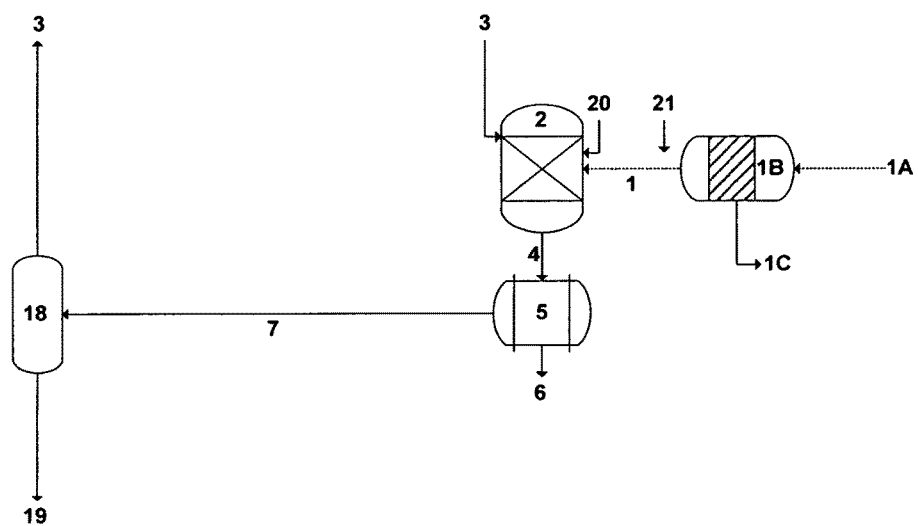
FIG. 6A illustrates a possible flow diagram for the invented method to de-oil and de-scale PW.

As mentioned above, PW from the Marcellus basin, for example, is a sulfate-depleted chloride type. However, the range of ions concentrations varies widely (e.g., Table 1). In some cases, the concentrations of alkaline cations in PW are relatively low, particularly barium and radium. In such cases wherein the concentrations of alkaline cations in PW are relatively low, the hydroxide route may be employed to precipitate such alkaline cations in a single stage, along with foulants, and (if desired) bromide. Foulants comprise transition metals, radium's decay series (also known as Naturally Occurring Radioactive Materials; NORM), sulfates, carbonates, boron, selenium, silica, and combinations thereof. Transition (heavy) metals comprise iron, manganese, aluminum, nickel, copper, zinc, cadmium, arsenic, chromium, mercury, lead, vanadium and combinations thereof. FIG. 6A depicts this inventive method using the hydroxide route to treat PW.

Humic acids, upon adding a hydroxide source, precipitate as agglomerates of their molecules. Such agglomerates bound some divalent and trivalent cations. The preferential binding of the back-end alkaline cations (strontium, barium and radium) by humic acid using an amine solvent as a hydroxide source at a mildly basic conditions (pH is at or about 9) was tested in my experiments and found to be very effective in precipitating such back-end alkaline cations. An inorganic-based hydroxide source, such as magnesium hydroxide, calcium hydroxide, sodium hydroxide and the like, may also be used in conjunction with humic acid. However, this necessitates the addition of a further source of ions, which may be undesirable since the purpose of treating PW is removing, rather than adding, ions. On the other hand, the selected amine solvents as a hydroxide source in this invention are very effective in inducing precipitation of targeted species within a very short period, and yet recoverable and recyclable for reuse in the process.

As illustrated in FIG. 6A, a readily de-oiled PW [1] may be fed to a precipitator unit [2] where it is inter-mixed with an amine solvent [3] as a hydroxide source and humic acid [20] to form precipitates comprising alkaline cations (magnesium, calcium, strontium, barium and radium hydroxides) and foulants. The amine solvent is selected from the group consisting of isopropylamine, propylamine, dipropylamine, diisopropylamine, ethylamine, diethylamine, methylamine, dimethylamine, and combinations thereof. Ammonia can also be used as a hydroxide source in this invention. Leonardite, for example, which predominantly comprises humic acid (e.g., >80%) as well as some fulvic acid, may be used as an inexpensive source of humic acid. A decanted and dissolved feed stock of the humic acid [20] can be made by rigorously mixing leonardite with water.

Bromide in PW can be converted to hypobromite by disinfecting PW, as shown in FIG. 6A, with an oxidizing agent [21]. The oxidizing agent comprises sodium hypochlorite, calcium hypochlorite and combinations thereof. Hypobromite can then be precipitated within alkaline cations in the precipitator unit [2] under the same basic conditions. My testing results indicated a high removal level (e.g., 95-99%) of bromide from PW.

The outlet stream [4] from the precipitator unit [2] is fed to a filter [5] to separate precipitates [6] and produce de-scaled PW [7]. The filter [5] may be equipped with a solvent recovery (not shown in FIG. 6A) to recover at least a portion of the amine solvent from the precipitates [6] (for recycling and reusing in the precipitator unit). The de-scaled PW [7] is fed to a stripping unit [18] to recover at least a portion of the amine solvent (for recycling and reusing in the precipitator unit), and produce treated PW [19].

Figure 6B:
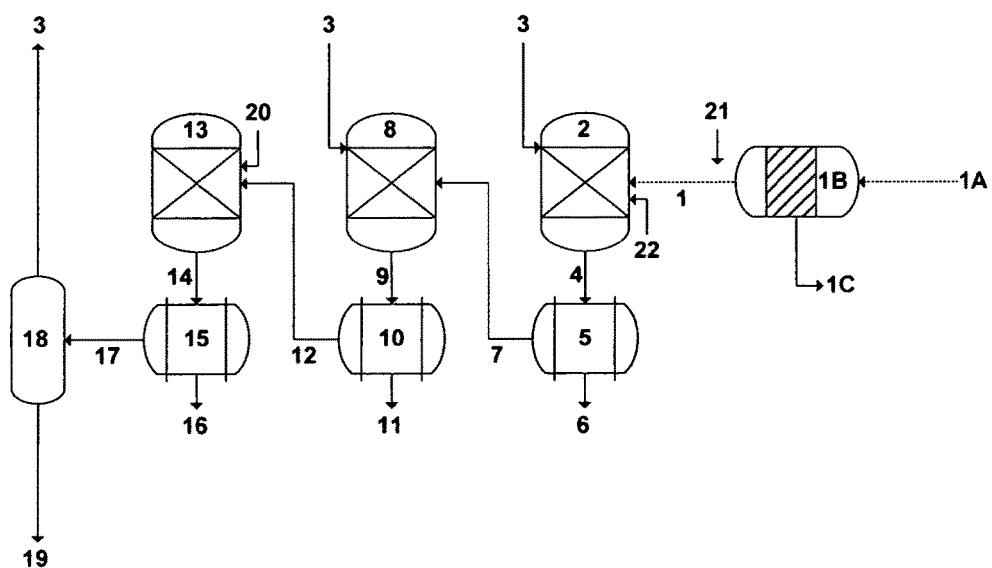
FIG. 6B illustrates a possible alternative flow diagram for the invented method to de-oil and de-scale PW.

FIG. 6B depicts an alternative de-scaling method to treat PW from the Marcellus basin (Table 1) and the like wherein the concentrations of the back-end alkaline cations (strontium, barium and radium) are high. Here, multi-precipitation stages may be required to effectively and selectively de-scale PW. The first precipitation stage is aimed at the selective precipitation of barium and radium sulfates along with foulants. As shown in FIG. 6B, a readily de-oiled PW [1] is inter-mixed with an amine solvent [3] and a sulfate source [22] in a first precipitator unit [2] to form first precipitates comprising barium and radium sulfates, and foulants. The sulfate source is a compound comprises sulfate, a stream comprises sulfate, and combinations thereof. Examples of sulfate-based compounds include, but not limited to, magnesium sulfate, calcium sulfate, sodium sulfate, potassium sulfate, and the like. Examples of sulfate-rich streams include, but not limited to, mine drainage water, spent water from flue gas scrubbers, agricultural drainage water, effluent streams from wastewater treatment plants, reject streams from advanced wastewater treatment plants, and the like. For example, mine drainage water (Table 4) and spent water from flue gas scrubbers are within the proximity of the Marcellus basin. The outlet stream [4] from the first precipitator unit [2] is fed to a first filter [5] to separate the first precipitates [6] and produce first de-scaled PW [7]. The first filter [5] may be equipped with a solvent recovery (not shown in FIG. 6B) to recover at least a portion of the amine solvent from the first precipitates [6].

As shown in FIG. 6B, the second precipitation stage is aimed at selectively precipitating magnesium from the first de-scaled PW [7]. The first de-scaled PW [7] is thus fed to a second precipitator unit [8] where it is inter-mixed with a further amount of the amine solvent [3] to form second precipitates comprising magnesium hydroxide. Bromide can also be co-precipitated with magnesium hydroxide in the second precipitator unit [8] upon disinfecting PW [1] with an oxidizing agent [21]. The outlet stream [9] from the second precipitator unit [8] is then fed to a second filter [10] to separate the second precipitates [11] and produce second de-scaled PW [12]. The second filter [5] may also be equipped with a solvent recovery (not shown in FIG. 6B) to recover at least a portion of the amine solvent from the second precipitates [11].

As shown in FIG. 6B, the third precipitation stage targets the selective separation of strontium from the second de-scaled PW [12]. The second de-scaled PW [12] is thus fed to a third precipitator unit [13] where it is inter-mixed with humic acid [20] to form third precipitates comprising strontium hydroxide. Here, the carried over amine solvent as a hydroxide source within the second de-scaled PW [12] may be sufficient to precipitate strontium. A further amount of the amine solvent [3] (not shown in FIG. 6B), if needed, can be introduced to the third precipitator unit [13]. The outlet stream [14] from the third precipitator unit [13] is then fed to a third filter [15] to separate the third precipitates [16] and produce third scaled PW [17]. The third filter [15] may also be equipped with a solvent recovery (not shown in FIG. 6B) to recover at least a portion of the amine solvent from the third precipitates [16]. The third de-scaled PW [17] is then fed to a stripping unit [18] to recover at least a portion of the amine solvent (for recycling and reusing in the precipitator units), and produce treated PW [19].

Figure 6C:
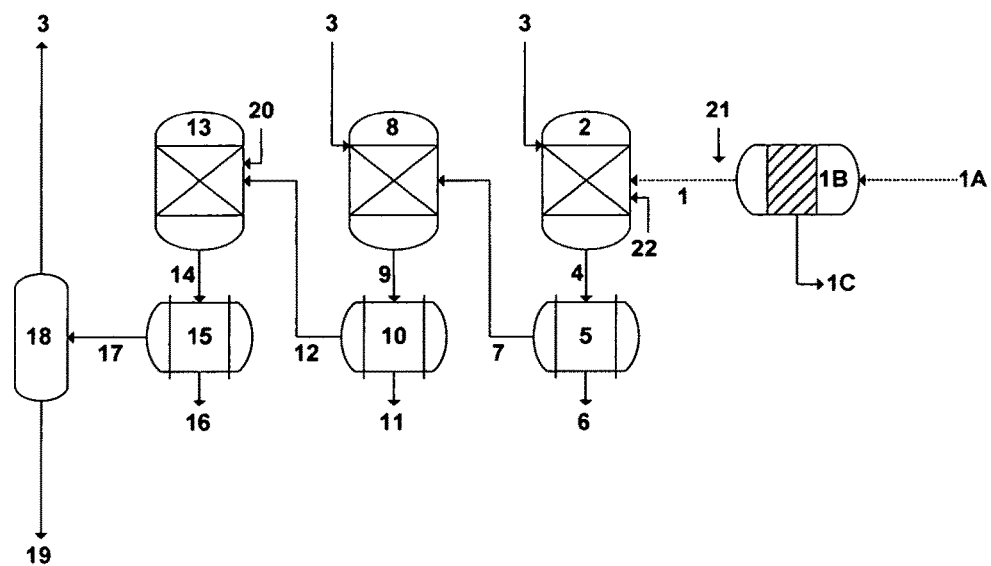
FIG. 6C illustrates another possible alternative flow diagram for the invented method to de-oil and de-scale PW.

As also mentioned above, PW from the Barnett basin distinctly differ from that in the Marcellus basin in: (1) the concentrations of the back-end alkaline cations (strontium, barium and radium), especially barium and radium, are low; and (2) the concentration of sulfate nearly matches (in terms of meq./L) the concentrations of the back-end alkaline cations (strontium, barium and radium). Thus, FIG. 6C depicts a further alternative de-scaling method to treat PW from the Barnett basin (Table 2) and the like wherein the concentrations of the back-end alkaline cations (especially barium and radium) are low and yet sulfate is available within PW. As such, the first precipitation stage is aimed at the selective precipitation of barium and radium sulfates along with foulants. As shown in FIG. 6C, a readily de-oiled PW [1] is inter-mixed with an amine solvent [3] in a first precipitator unit [2] to form first precipitates comprising barium and radium sulfates along with foulants. Here, a small portion of the sulfate concentration within PW is utilized to precipitate barium and radium. The outlet stream [4] from the first precipitator unit [2] is fed to a first filter [5] to separate the first precipitates [6] and produce first de-scaled PW [7]. The first filter [5] may be equipped with a solvent recovery (not shown in FIG. 6C) to recover at least a portion of the amine solvent from the first precipitates [6].

The second precipitation stage, as shown in FIG. 6C, is aimed at selectively precipitating magnesium from the first de-scaled PW [7]. The first de-scaled PW [7] is thus fed to a second precipitator unit [8] where it is inter-mixed with a further amount of the amine solvent [3] to form second precipitates comprising magnesium hydroxide. Bromide can also be co-precipitated with magnesium hydroxide in the second precipitator unit [8] upon disinfecting PW [1] with an oxidizing agent [21]. The outlet stream [9] from the second precipitator unit [8] is then fed to a second filter [10] to separate the second precipitates [11] and produce second de-scaled PW [12]. The second filter [5] may also be equipped with a solvent recovery (not shown in FIG. 6C) to recover at least a portion of the amine solvent from the second precipitates [11].

The third precipitation stage, as shown in FIG. 6C, targets the selective separation of strontium from the second de-scaled PW [12]. The second de-scaled PW [12] is thus fed to a third precipitator unit [13] where it is inter-mixed with humic acid [20] to form third precipitates comprising strontium hydroxide. The carried over amine solvent as a hydroxide source within the second de-scaled PW [12] may be sufficient to precipitate strontium. A further amount of the amine solvent [3] (not shown in FIG. 6C), if needed, can be introduced to the third precipitator unit [13]. The outlet stream [14] from the third precipitator unit [13] is then fed to a third filter [15] to separate the third precipitates [16] and produce third scaled PW [17]. The third filter [15] may also be equipped with a solvent recovery (not shown in FIG. 6C) to recover at least a portion of the amine solvent from the third precipitates [16]. The third de-scaled PW [17] is fed to a stripping unit [18] to recover at least a portion of the amine solvent (for recycling and reusing in the precipitator units), and produce treated PW [19].

Figure 6D:
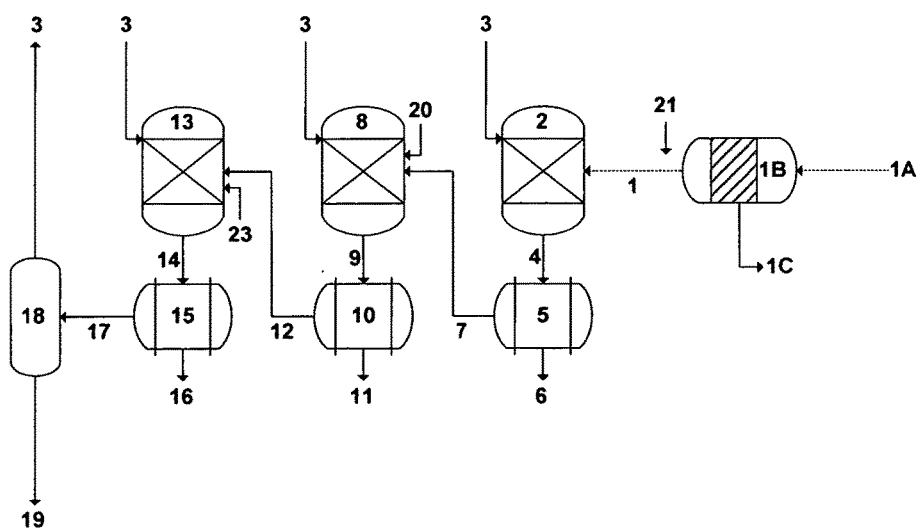
FIG. 6D illustrates a further possible alternative flow diagram for the invented method to de-oil and de-scale PW.

Yet, FIG. 6D depicts a further alternative de-scaling method to treat PW from the Barnett basin (Table 2) and the like wherein the concentrations of the back-end alkaline cations (especially barium and radium) are low and yet sulfate is available within PW. As shown in FIG. 6D, the first precipitation stage, which is aimed at the selective precipitation of barium and radium sulfates along with foulants, is identical to the first precipitation stage [1 to 7] as given in FIG. 6C and described above. However, the second precipitation stage, as shown in FIG. 6D, is aimed at selectively precipitating magnesium and strontium from the first de-scaled PW [7]. The first de-scaled PW [7] is thus fed to a second precipitator unit [8] where it is inter-mixed with a further amount of the amine solvent [3] and humic acid [20] to form second precipitates comprising magnesium and strontium hydroxides. Bromide can also be co-precipitated with magnesium and strontium hydroxides in the second precipitator unit [8] upon disinfecting PW [1] with an oxidizing agent [21]. The outlet stream [9] from the second precipitator unit [8] is then fed to a second filter [10] to separate the second precipitates [11] and produce second de-scaled PW [12]. The second filter [5] may also be equipped with a solvent recovery (not shown in FIG. 6D) to recover at least a portion of the amine solvent from the second precipitates [11].

The third precipitation stage, as shown in FIG. 6D, targets the selective separation of sulfate from the second de-scaled PW [12]. The median concentration of calcium (meq./L) is over 5-fold higher than the median concentration of sulfate in PW from the Barnett basin (Table 2). As such, sulfate and calcium can be separated together in the third precipitation stage as calcium sulfoaluminate or calcium sulfoferrate upon adding an aluminum source or an iron source along with a hydroxide source. The second de-scaled PW [12] is thus fed to a third precipitator unit [13] where it is inter-mixed with the amine solvent [3], and either aluminum hydroxide or iron hydroxide [23] to form third precipitates comprising either calcium sulfoaluminate or calcium sulfoferrate. The outlet stream [14] from the third precipitator unit [13] is then fed to a third filter [15] to separate the third precipitates [16] and produce third scaled PW [17]. The third filter [15] may also be equipped with a solvent recovery (not shown in FIG. 6D) to recover at least a portion of the amine solvent from the third precipitates [16]. The third de-scaled PW [17] is fed to a stripping unit [18] to recover at least a portion of the amine solvent (for recycling and reusing in the precipitator units), and produce treated PW [19].

Figure 6E:
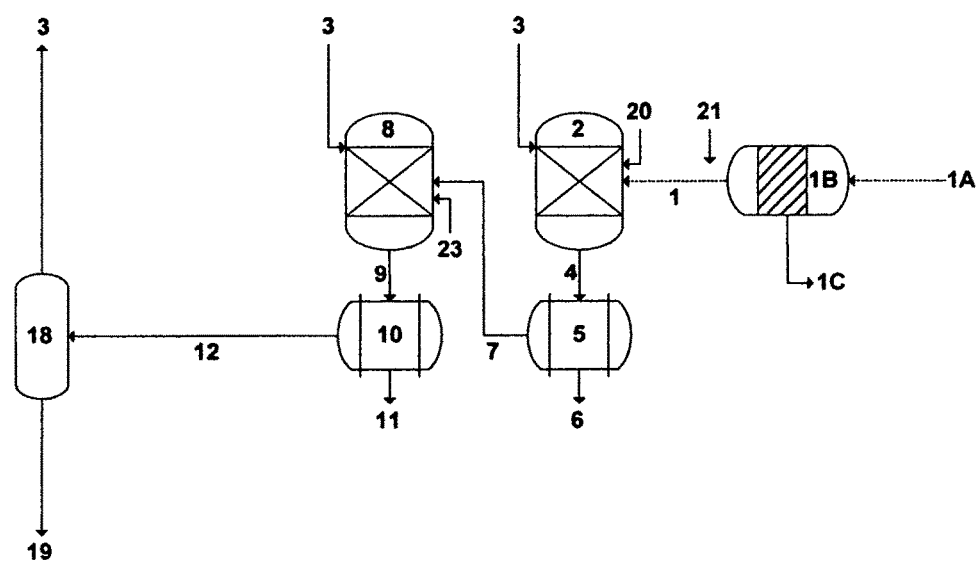
FIG. 6E illustrates yet a further possible alternative flow diagram for the invented method to de-oil and de-scale PW.

Yet, FIG. 6E depicts a further alternative de-scaling method, wherein the precipitation stages are reduced to two stages, to treat PW from the Barnett basin (Table 2) and the like wherein the concentrations of the back-end alkaline cations (especially barium and radium) are low and yet sulfate is available within PW. Here, the first precipitation stage is aimed at the selective precipitation of barium and radium sulfates, magnesium and strontium hydroxides, and foulants. As shown in FIG. 6E, a readily de-oiled PW [1] is inter-mixed with an amine solvent [3] and humic acid [20] in a first precipitator unit [2] to form first precipitates comprising barium and radium sulfates, magnesium and strontium hydroxides, along with foulants. Bromide can also be co-precipitated with the first precipitates in the first precipitator unit [2] upon disinfecting PW [1] with an oxidizing agent [21]. A small portion of the sulfate concentration within PW is utilized to precipitate barium and radium. The outlet stream [4] from the first precipitator unit [2] is fed to a first filter [5] to separate the first precipitates [6] and produce first de-scaled PW [7]. The first filter [5] may be equipped with a solvent recovery (not shown in FIG. 6E) to recover at least a portion of the amine solvent from the first precipitates [6].

The second precipitation stage, as shown in FIG. 6E, targets the selective separation of sulfate from the first de-scaled PW [7]. Since the median concentration of calcium (meq./L) is over 5-fold higher than the median concentration of sulfate in PW from the Barnett basin (Table 2), sulfate and calcium can be separated together in the second precipitation stage as calcium sulfoaluminate or calcium sulfoferrate upon adding an aluminum source or an iron source along with a hydroxide source. The first de-scaled PW [7] is thus fed to a second precipitator unit [8] where it is inter-mixed with the amine solvent [3], and either aluminum hydroxide or iron hydroxide [23] to form second precipitates comprising either calcium sulfoaluminate or calcium sulfoferrate. The outlet stream [9] from the second precipitator unit [8] is then fed to a second filter [10] to separate the second precipitates [11] and produce second scaled PW [12]. The second filter [10] may also be equipped with a solvent recovery (not shown in FIG. 6E) to recover at least a portion of the amine solvent from the second precipitates [11]. The second de-scaled PW [12] is fed to a stripping unit [18] to recover at least a portion of the amine solvent [3] (for recycling and reusing in the precipitator units), and produce treated PW [19].

The precipitation of calcium sulfoaluminate or calcium sulfoferrate takes place based on the conditions under which it is effectively precipitated. Based on the inventor's testing, the removal of sulfate from PW in the form of either calcium sulfoaluminate or calcium sulfoferrate is consistently over 97%. One structural formula that may generally describe certain embodiments of calcium sulfoaluminate or calcium sulfoferrate is as follows:

$$[Ca^{+2}]_A[SO_4^{-2}]_B[M^{+3}]_C[xH_2O] \quad (14)$$

where A is the stoichiometric amount of calcium ($Ca^{+2}$), B is stoichiometric amount of sulfate ($SO^2$), C is the stoichiometric amount of the trivalent cation ($M^{+3}$; which is either aluminum: $Al^{+3}$ or iron: $Fe^{+3}$), and x is the hydration content. Depending on the amounts of sulfate and calcium in PW, the chemistry of PW, and the basicity condition under which sulfate is precipitated in the form of either calcium sulfoaluminate or calcium sulfoferrate, the stoichiometric ratio (meq./L) of sulfate to calcium (B/A) may be 0.1 to 0.5, the stoichiometric ratio (meq./L) of sulfate to the trivalent cation (B/C) may be 0.5 to 1.5, and the hydration content (x) may be 24 to 32.

It should be noted that further arrangements for the precipitation stages in this invention can be envisioned.

It should be understood that the above described de-scaling methods are equally applicable to treat source water comprises, but not limited to, all kinds of mine drainage water, spent water from flue gas scrubbers, agricultural drainage water, effluent streams from wastewater treatment plants, reject streams from advanced wastewater treatment plants, radioactive waste streams, and combinations thereof.

The Inventive De-Oiling/De-Watering Methods

As shown in FIGS. 6A to 6E, PW [1A] is alternatively treated by the inventive hydrophobic membranes [1B], prior to conducting the inventive de-scaling methods as described above, to simultaneously produce de-oiled PW [1] and de-watered oil [1C].

Dissolved humic acid (not shown in FIGS. 6A to 6E), without the present of a hydroxide source, can also mixed to PW [1A] prior to conducting the inventive hydrophobic membranes [1B] to de-oil PW [1] and de-water oil [1C]. As explained in paragraphs [0062] and [0063], the main oil-water interactions include: (1) ion hydration between charged organic groups (e.g., oxygen-, nitrogen-, and sulfur-containing species); (2) hydrogen bonding between polar organic groups and water; and (3) hydrophobic hydration (e.g., neutral organic groups). Upon mixing dissolved humic acid with PW, humic acid, as a negatively charged matrix, sorbs positively charged organic species, withdraws various chains of negatively charged organic species through neutralizing and bridging interactions, and produces a contracted, micelle-like hydrophobic microenvironment, with a relatively non-polar interior (comprising neutral organic species such as benzene and the like) and a polar surface. Thus, hydrophobic species partition into these regions, are isolated there, and are carried over to be effectively separated by the hydrophobic membranes [1B] as readily de-watered oil [1C], thereby producing readily de-oiled PW [1].

It should be noted that if bromide is targeted for precipitation by the inventive de-scaling methods as given in FIGS. 6A to 6E and described above and the inventive de-oiling/de-watering methods by hydrophobic membranes [1B] are implemented in conjunction with the de-scaling methods, the oxidizing agent [21] may be alternatively mixed with PW [1A] upstream of such hydrophobic membranes [1B].

The Inventive De-Salting Methods

The treated PW [19] (FIGS. 6A to 6E) may be de-salted by any known de-salting (desalination) method. However, the combination of the multistage flash principle with the vapor compression principle is desirable but has not been attained in a practical manner. This invention recognizes the need for combining such principles to provide effective, simple, flexible and economical de-salting (desalination) methods.

Figure 7:
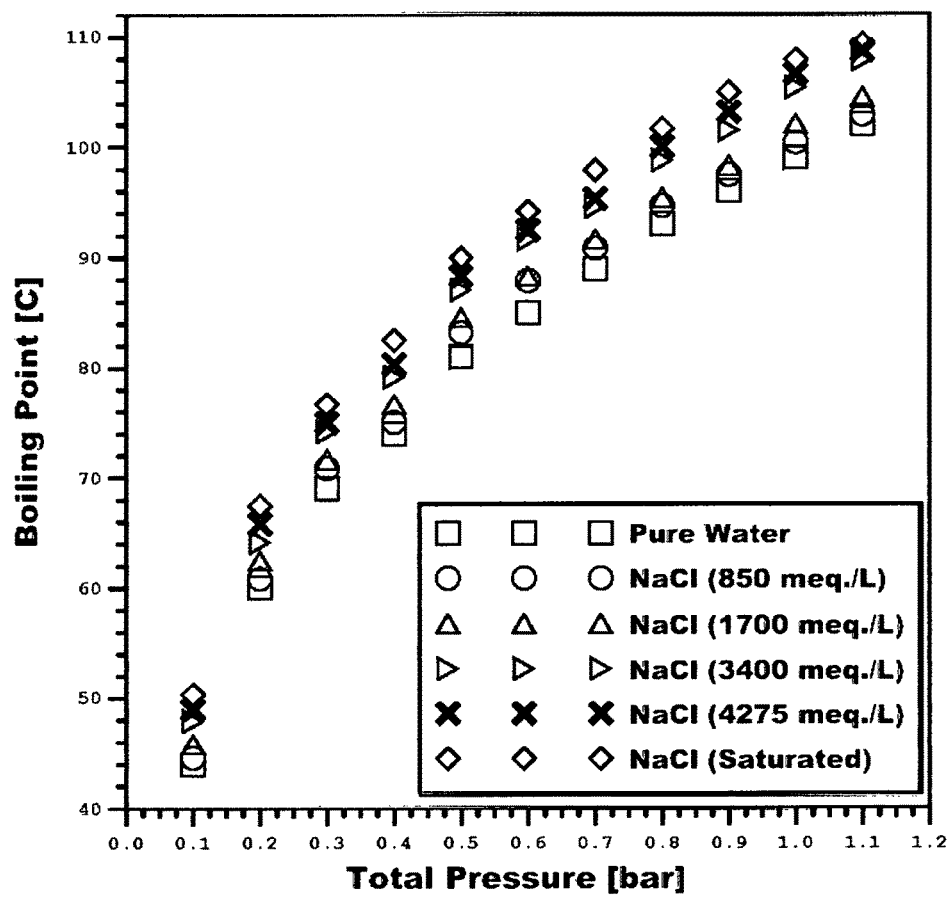
FIG. 7 illustrates the boiling points of pure water and water containing sodium chloride versus total pressures.

Boiling occurs when the vapor pressure of water is equal to the total pressure on the water surface. FIG. 7 shows the boiling points of pure water and water containing sodium chloride (an approximation to a saline stream or a concentrated saline stream) at different concentrations as a function of total pressures. Under atmospheric pressure (1.01 bar), pure water boils at 100° C. whereas water saturated with sodium chloride boils at 109.5° C. On the other hand, pure water boils at 44° C. and water saturated with sodium chloride boils at 50.3° C. under a total pressure of 0.1 bar absolute. When pressure is reduced, the boiling point is correspondingly reduced. As such, vapor can be produced from water (liquid) when water is at its boiling point, either by directly adding heat (boiling) or by reducing pressure (flashing).

Figure 8A:
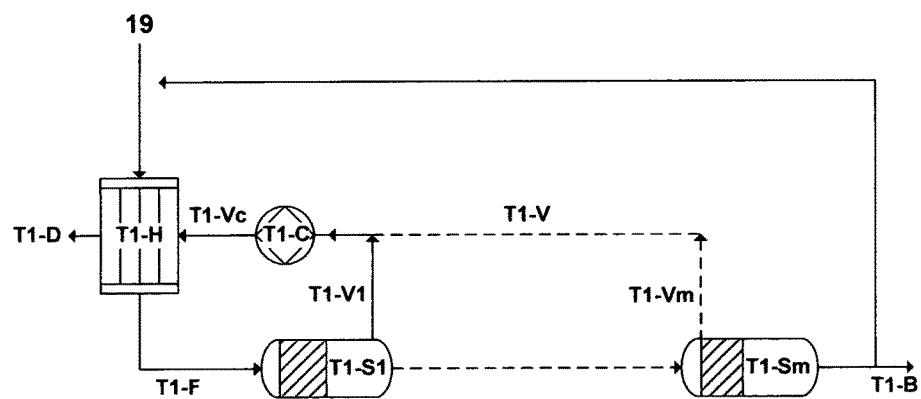
FIG. 8A illustrates a possible flow diagram for the inventive de-salting train to de-salt PW.

FIG. 8A illustrates, as an example, an oversimplified flow diagram for the inventive method for desalinating treated PW [19] by combining the multi-stage flash and vapor compression principles in a desalination train. The inventive method, as shown in FIG. 8A, comprising a desalination train wherein the desalination train comprises at least a heat exchanger [T1-H], a plurality of flashing stages arranged in series [T1-S1 to T1-Sm] and at least a compression device [T1-C]. Here, the desalination train is based on flashing stages arranged in series, wherein each flashing stage possesses a lower pressure to lower the boiling point of source water than a preceding flashing stage. This allows successive reduction of the boiling point of water as it gets more concentrated in going down the flashing stages.

The notations "T1", "T1-H", "T1-S1 to T1-Sm", "T1-F", "T1-V1 to T1-Vm", "T1-C", "T1-V", "T1-Vc", "T1-D" and "T1-B" refer to, respectively, the desalination train, the heat exchanger of the desalination train, the number of flashing stages in the desalination train, the heated source water to feed the first flashing stage of the desalination train, the flashed vapor in each of the flashing stages of the desalination train, the compression device of the desalination train, the withdrawn vapor from the flashing stages of the desalination train, the compressed vapor by the compression device of the desalination train, the produced distillate of the desalination train, and reject brine of the desalination train.

To increase the thermal efficiency (heat recovery) of this single desalination train (FIG. 8A), the number of flashing stages can be increased. As such, the number of flashing stages [S1 to Sm] in series can be extended from "1" to "m" stages, which indicated in FIG. 8A by dotted lines. The pressure in each flashing stage is lower than the pressure in a preceding flashing stage. The minimum pressure and temperature in a last flashing stage ("Sm") of the desalination train are dictated at least by the volume of recoverable vapor and heat rejection considerations of reject brine. The number of flashing stages thus controls the amount of heat recovery possible within the desalination train, which, in turn, controls the amount of external energy required (thereby the size of the compression device). Here, the compressor device serves as an open system "heat pump" that requires only enough energy to compress the vapor since it continuously reuses latent heat.

As shown in FIG. 8A, treated PW [19] (resulting from the above described de-scaling methods as given in FIGS. 6A to 6E) to be desalinated is fed through the heat exchanger [T1-H] and then [T1-F] in succession through the flashing stages [T1-S1 to T1-Sm] to bring water to a vaporizing temperature by maintaining the flashing stages at progressively lower pressures in the direction of going down the flashing stages (from T1-S1 to T1-Sm), thereby water at saturation temperature corresponding to the pressure in a flashing stage flows to a next succeeding flashing stage at a lower pressure and arrives in the next flashing stage at a temperature higher than the saturation temperature corresponding to the lower pressure in the next flashing stage so that at least a portion of water flashes into vapor [T1-V1 to T1-Vm] in each of the flashing stages [T1-S1 to T1-Sm]. The vapor [T1-V1 to T1-Vm] from each of the flashing stages is withdrawn, and at least a portion of the withdrawn vapor [T1-V] is compressed by the compression device [T1-C]. The compressed vapor [T1-Vc] is condensed in the heat exchanger [T1-H], thereby producing distillate [T1-D] as well as heating source water [1] before entering [T1-F] a first flashing stage [T1-S1] of the desalination train. Here, the latent heats of heating and condensing fluids are nearly completely equal. Thus, the sensible heat of the compressed vapor [T1-V] upon cooling in the heat exchanger [T1-H] is converted to latent heat, and upon condensation on the tubes of the heat exchanger [T1-H] (to produce distillate [T1-D]) is added as sensible heat to source water [T1-F]. Unflashed water (brine) is rejected from a last flashing stage [T1-Sm] of the desalination train as reject brine [T1-B].

The flashing stages [T1-S1 to T1-Sm] comprise hydrophobic membranes under reduced pressure.

The flashing stage [T1-S1 to T1-Sm] further comprise simple vapor-liquid separators (flash tanks) under reduced pressure, wherein the vapor-liquid separators comprise hydrophobic demister pads. Here, hydrophobic membranes (hydrophobic demister pads) capture water droplets that entrain with flashed vapor.

The compression device [C-1] is selected from the group consisting of a mechanically driven compression device, a thermally driven compression device, and combinations thereof.

Reject brine [T1-B] further comprises the step of recycling at least a portion of reject brine [T1-B] for mixing with treated PW [19] prior to entering the heat exchanger [T1-H].

Figure 8B:
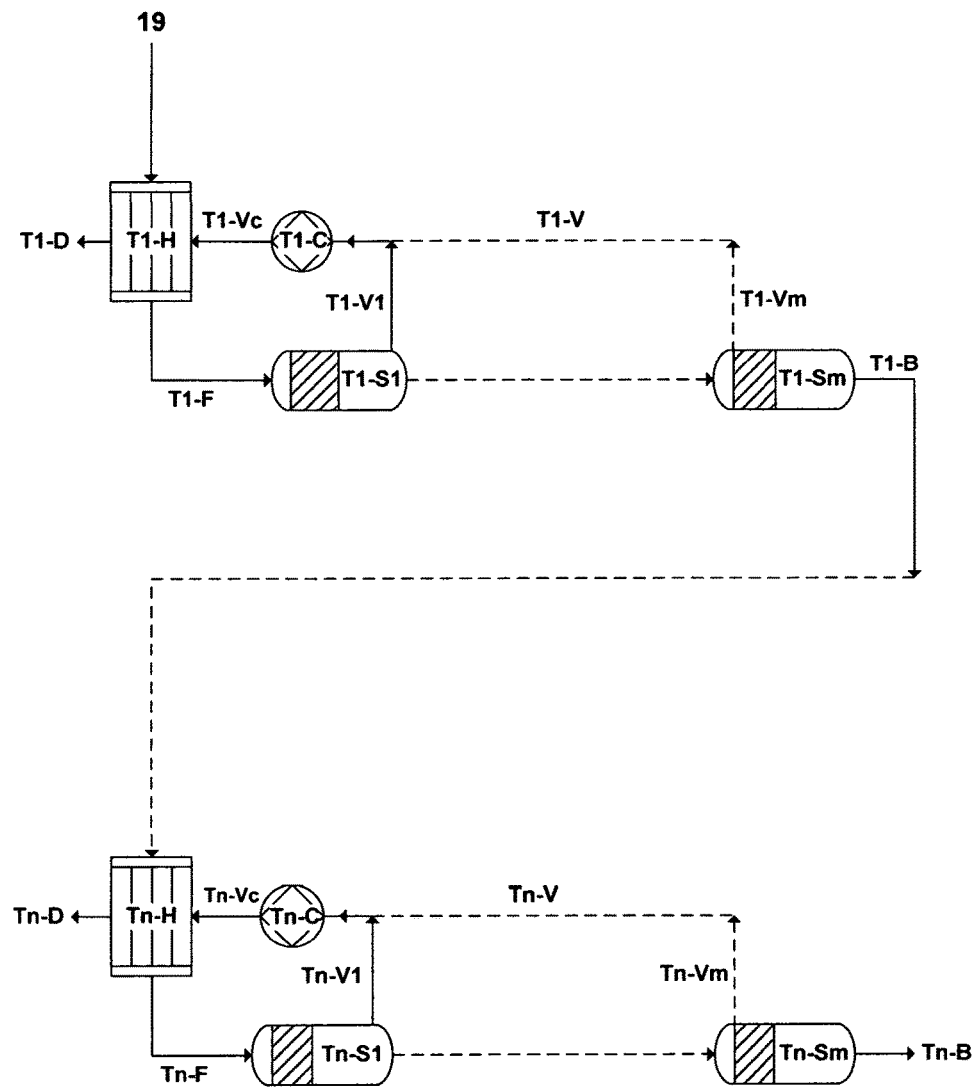
FIG. 8B illustrates a possible flow diagram for the inventive Brine-Forward (BF) de-salting system to de-salt PW.

The inventive desalination train as given in FIG. 8A and described above further comprises interrelating a plurality of such a desalination train in what I coined a brine-forward desalination system as shown in FIG. 8B. The inventive brine-forward desalination system comprises a plurality of desalination trains arranged in series, in which each of the desalination train, as described above, comprises at least a heat exchanger, plurality of flashing stages arranged in series, and at least a compression device. As such, the number of desalination trains [T1 to Tn] in series can be extended from "1" to "n" trains, which indicated in FIG. 8B by dotted lines. For example, the last desalination train, as shown in FIG. 8B, comprises at least a heat exchanger [Tn-H], a plurality of flashing stages arranged in series [Tn-S1 to Tn-Sm], and at least a compression device [Tn-C].

Each of the desalination train produces distillate and reject brine (as given in FIG. 8A and described above). However, reject brine from each of the desalination train except a last desalination train in the brine-forward desalination system passes through to feed a next succeeding desalination train, thereby each of the desalination train progressively possesses a higher level of total dissolved solids (TDS) than a preceding desalination train, and reject brine from the last desalination train in the brine-forward desalination system may be rejected at a level not exceeding 250,000 mg/L of TDS. Treated PW [19] (effectively de-scaled as given in FIGS. 6A to 6E and described above) would facilitate the rejection of brine from the last desalination train at a TDS level of about 250,000 mg/L since the treated PW would contain nearly sodium chloride or sodium-calcium chloride. De-scaling, as provided by inventive de-scaling methods (FIGS. 6A to 6E), thus controls the number of desalination trains in the brine-forward desalination system, which, in turn, controls the volume and TDS level of reject brine resulting from the brine-forward desalination system. As such, the inventive brine forward desalination system is a multi-flashing system without supplying additional heat after a heat exchanger of each desalination train, and a multi-concentration system without supplying additional treated PW after a heat exchanger of a first desalination train.

Figure 9A:
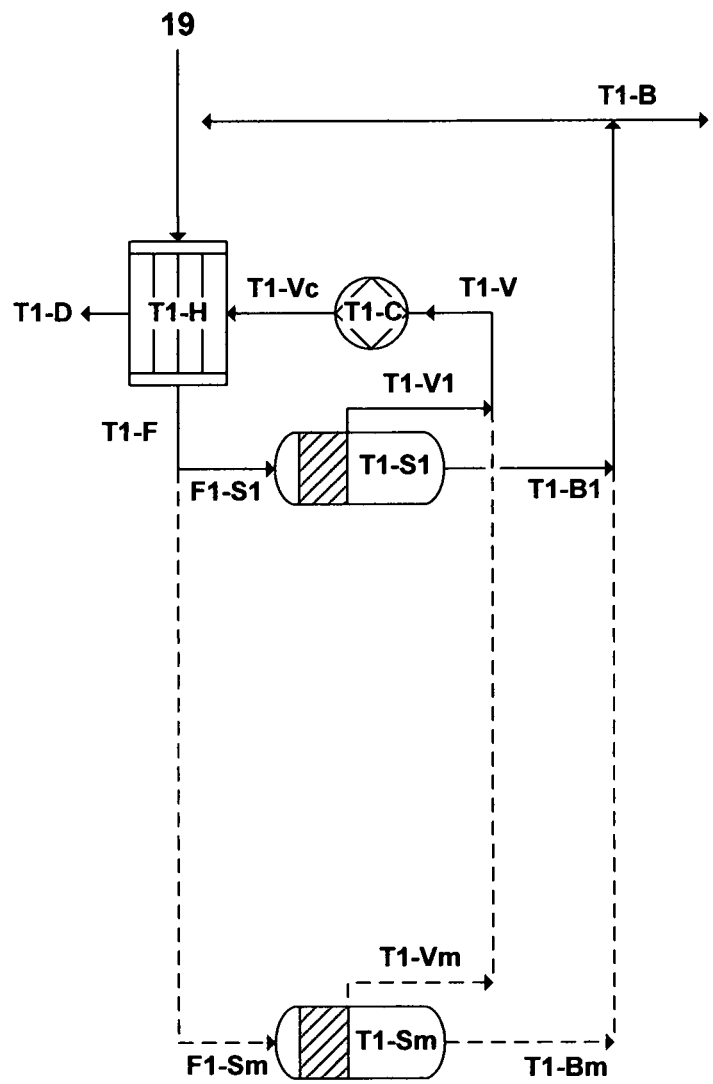
FIG. 9A illustrates another possible flow diagram for the inventive de-salting train to de-salt PW.

Alternatively, FIG. 9A illustrates another oversimplified flow diagram for the inventive method for desalinating source water by combining the multi-stage flash and vapor compression principles in a desalination train. The inventive method, as shown in FIG. 9A, comprising a desalination train wherein the desalination train comprises at least a heat exchanger [T1-H], a plurality of flashing stages arranged in parallel [T1-S1 to T1-Sm] and at least a compression device [T1-C]. Here, the desalination train is based on flashing stages arranged in parallel, thereby heated source water [T1-F] by the heat exchanger [T1-H] is distributed [F1-S to F1-Sm] among the flashing stages [T1-S1 to T1-Sm]. The flashing stages are, in turn, maintained at a lower pressure wherein water at saturation temperature corresponding to the low pressure in the flashing stages or at a temperature higher than the saturation temperature corresponding to the lower pressure in the flashing stages so that at least a portion of water flashes into vapor [T1-V1 to T1-Vm] in each of the flashing stages [T1-S1 to T1-Sm]. As such, the arrangement of the flashing stages in parallel: (1) reduces the amount of heat that has to be added to the desalination train via the compression device; and (2) allows maximizing vapor recovery from the flashing stages since no constraints (e.g., temperature drop in each flashing stage, and total flash range) on lowering the pressure in each flashing stage (unlike the arrangement of the flashing stages in series).

As shown in FIG. 9A, treated PW [19] to be desalinated is fed through the heat exchanger [T1-H] and then [T1-F] in parallel [F1-S1 to F1-Sm] through the flashing stages [T1-S1 to T1-Sm] to bring water to a vaporizing temperature by maintaining the flashing stages at a similar lower pressure wherein water at saturation temperature corresponding to the low pressure in the flashing stages or at a temperature higher than the saturation temperature corresponding to the lower pressure in the flashing stages so that at least a portion of water flashes into vapor [T1-V1 to T1-Vm] in each of the flashing stages [T1-S1 to T1-Sm]. The vapor [T1-V1 to T1-Vm] from each of the flashing stages is withdrawn, and at least a portion of the withdrawn vapor [T1-V] is compressed by the compression device [T1-C]. The compressed vapor [T1-Vc] is then condensed in the heat exchanger [T1-H], thereby producing distillate [T1-D] and heating source water [1] before entering [T1-F] each [F1-S1 to F1-Sm] of the flashing stages [T1-S1 to T1-Sm] of the desalination train. Unflashed water (brine) [T1-BI to T1-Bm] is rejected from each of the flashing stages [T1-S1 to T1-Sm] and combined as reject brine [T1-B] of the desalination train.

Figure 9B:
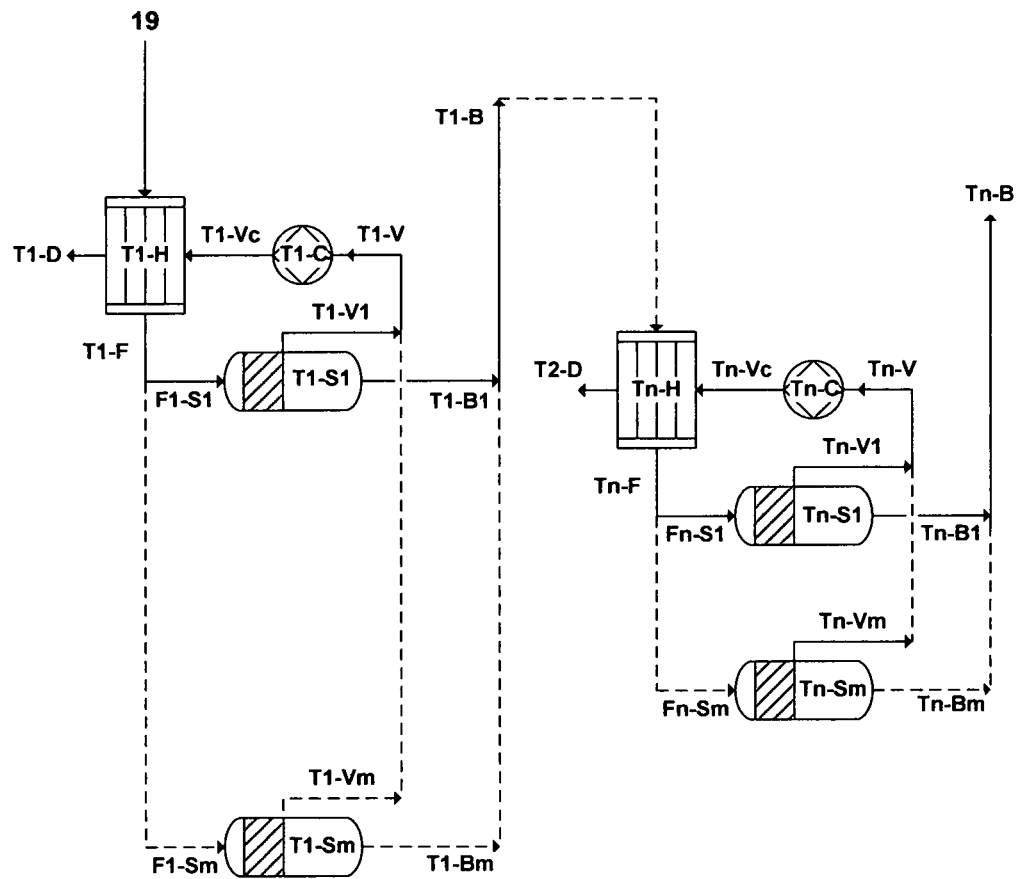
FIG. 9B illustrates another possible flow diagram for the inventive Brine-Forward (BF) de-salting system to de-salt PW.

The inventive desalination train as given in FIG. 9A and described above further comprises interrelating a plurality of desalination trains in what I coined a brine-forward desalination system as shown in FIG. 9B. The inventive brine-forward desalination system comprises a plurality of desalination trains arranged in series, in which each of the desalination train, as described above (FIG. 9A), comprises at least the heat exchanger, the plurality of flashing stages arranged in parallel, and at least the compression device. As such, the number of desalination trains [T1 to Tn] in series can be extended from "1" to "n" trains, which indicated in FIG. 9B by dotted lines. For example, the last desalination train, as shown in FIG. 9B, comprises at least a heat exchanger [Tn-H], a plurality of flashing stages arranged in parallel [Tn-S1 to Tn-Sm], and at least a compression device [Tn-C]. Each of the desalination train produces distillate and reject brine (as given in FIG. 9A and described above). However, reject brine from each of the desalination train except a last desalination train in the brine-forward desalination system passes through to feed a next succeeding desalination train, thereby each of the desalination train progressively possesses a higher level of total dissolved solids (TDS) than a preceding desalination train, and reject brine from the last desalination train in the brine-forward desalination system may be rejected at a level not exceeding 250,000 mg/L of TDS. Thus, the inventive brine forward desalination system is a multi-flashing system without supplying additional heat after a heat exchanger of each desalination train, and a multi-concentration system without supplying additional source water after a first heat exchanger of a first desalination train.

There are several distinct features for the inventive de-salting methods. First, the latent heat from the evaporation side (evaporating vapor) is recycled to the condensing side (the treated PW) of the desalination train. The invention aims at recovering the latent heat from evaporating vapor rather than rejecting this latent heat in cooling water or a water cooled condenser.

Second, the inventive de-salting methods also aim at eliminating or greatly reducing the use of steam as the primary heat energy. Instead, a compression device is utilized as a heat pump that can be driven mechanically (e.g., a fan, a blower, a compressor, or a combination), thermally (e.g., a steam jet), and combinations. The energy input required by the compression device is equal to the energy required to raise the vapor pressure (thereby the vapor saturation temperature) by an amount equivalent to the thermal driving force across the flashing stages. As such, the energy input per unit mass of distillate is low since it is mostly for driving the compression device, and the heat to be rejected from the inventive desalination train is also low since it is equal to the energy input of the compression device.

Third, the inventive de-salting methods with flashing stages comprise hydrophobic membranes operate at significantly lower temperatures (e.g., at or below 85° C.).

Fourth, the flashing stages in the inventive de-salting methods comprise hydrophobic membranes, which are characterized with ease of fabrication, modification and scale-up. Such inventive methods also operate at a significantly higher level of surface area to volume than any other de-salting method. These two factors lead to a dramatic reduction in size and cost of construction materials. A very large saving in the cost of producing distillate will thus result with the inventive de-salting methods since they are compact, modular, and made out of cheaper materials (e.g., polymers, inorganic composites (ceramic), and polymers and glass lining materials), which is in contrast to extensive alloy heat transfer tubes (e.g., copper-nickel, aluminum-brass, titanium, or a combination) and bulky alloy evaporators shells (e.g., duplex stainless steel, clad materials, etc.) in conventional thermally-driven de-salting methods.

TABLE 1

Samples of PW at Day 14 from the Marcellus Basin.

| Species | Concentration (mg/L) | |
|---|---|---|
| | Range | Median |
| $Na^+$ | 1,100-44,100 | 36,400 |
| $K^+$ | 8-1,010 | 281 |
| $Mg^{+2}$ | 22-1,800 | 875 |
| $Ca^{+2}$ | 204-14,800 | 11,200 |
| $Sr^{+2}$ | 46-5,350 | 2,330 |
| $Ba^{+2}$ | 76-13,600 | 1,990 |
| $Ra^{+2}$ (Total: Isotopes 226 and 228) | 73-6,540* | |
| $Fe^{+2}$ | 14-59 | 47 |
| $Mn^{+2}$ | 1.2-8.4 | 5.6 |
| $Zn^{+2}$ | 0.07-0.14 | 0.09 |
| $Al^{+3}$ | 0.15-0.91 | 0.5 |
| B | 2.7-3,880 | 20 |
| $Cl^-$ | 1,070-151,000 | 98,300 |
| $Br^-$ | 16-1,190 | 872 |
| $HCO_3^-$ | 26-95 | 71 |
| $SO_4^{-2}$ | 0.8-89 | <50 |
| Total Dissolved Solids (TDS) | 3,010-228,000 | 157,000 |
| Total Hardness (TH) | 600-44,407 | 31,596 |
| Oil & Grease (O&G) | 7.4-103 | 30.8 |
| Chemical Oxygen Demand (COD) | 28-128,000 | 8,370 |
| pH | 5.8-6.6 | 6.2 |

*pCi/L;
Oil & Grease (O&G) based on U.S. EPA Method 1664 is Total Oil Content (TOC).

TABLE 2

Samples of PW at Day 10-12 from the Barnett Basin.

| Species | Concentration (mg/L) | |
|---|---|---|
| | Range | Median |
| $Na^+$ | 4,370-28,200 | 18,850 |
| $K^+$ | 80-750 | 316 |
| $Mg^{+2}$ | 149-755 | 255 |
| $Ca^{+2}$ | 1,110-6,730 | 1,600 |
| $Sr^{+2}$ | 48-1,550 | 529 |
| $Ba^{+2}$ | 0.93-17.9 | 3.6 |
| $Ra^{+2}$ | | |
| $Fe^{+2}$ | 12.1-93.8 | 24.9 |
| $Mn^{+2}$ | 0.25-2.20 | 0.86 |
| $Zn^{+2}$ | 0.10-0.36 | 0.15 |
| $Al^{+3}$ | 0.37-2.21 | 0.43 |
| B | 7.0-31.9 | 30.3 |
| $Cl^-$ | 9,600-60,800 | 34,700 |
| $Br^-$ | 117-798 | 589 |
| $HCO_3^-$ | 215-1,240 | 725 |
| $SO_4^{-2}$ | 120-1,260 | 709 |
| Total Dissolved Solids (TDS) | 16,400-97,800 | 50,550 |
| Total Hardness (TH) | 3,500-21,000 | 5,800 |
| Oil & Grease (O&G) | 88.2-1,430 | 163.5 |
| Chemical Oxygen Demand (COD) | 927-3,150 | 2,945 |
| pH | 6.5-7.2 | 7.05 |

TABLE 3

Some Relevant Properties of Alkaline Cations.

| Alkaline Cation | Atomic Number | Charge Density | Hydrated Radius (A°) | Ionic Radius (A°) | Polarizability ($A^{o3}$) |
|---|---|---|---|---|---|
| $Mg^{+2}$ | 12 | 3.01 | 4.28 | 0.65 | 10.6 |
| $Ca^{+2}$ | 20 | 2.02 | 4.12 | 0.98 | 22.8 |
| $Sr^{+2}$ | 38 | 1.77 | 4.12 | 1.16 | 27.6 |
| $Ba^{+2}$ | 56 | 1.48 | 4.04 | 1.36 | 39.7 |
| $Ra^{+2}$ | 88 | 1.32 | | 1.43 | 38.3 |

TABLE 4

Samples of Mine Drainage Water (Coal Mines) in Pennsylvania.

| Species | Range of Concentrations (mg/L) |
|---|---|
| "Distinctly Acidic" Mine Drainage Water | |
| $Mg^{+2}$ | 39-225 |
| $Ca^{+2}$ | 65-190 |
| $Fe^{+2}$ | 74-1,560 |
| $Mn^{+2}$ | 34-120 |
| $Al^{+3}$ | 24-270 |
| $SO_4^{-2}$ | 1,800-7,600 |
| pH | 1.9-2.6 |
| "Mildly Acidic to Neutral" Mine Drainage Water | |
| $Mg^{+2}$ | 9-130 |
| $Ca^{+2}$ | 27-140 |
| $Fe^{+2}$ | 5-260 |
| $Mn^{+2}$ | 4-49 |
| $Al^{+3}$ | 0.3-28 |
| $SO_4^{-2}$ | 680-3,400 |
| pH | 3.8-7.6 |

What is claimed is:

1. A method for treating an oil-water stream, said method comprising mixing said oil water stream with humic acid; wherein said humic acid sorbs positively charged organic species, withdraws negatively charged organic species through neutralizing and bridging interactions, and produces partitioned hydrophobic species with an inner core containing neutral organic species; separating said partitioned hydrophobic species in said oil-water stream by a hydrophobic membrane to produce a de-watered oil stream, and a de-oiled water stream; and recognizing that said oil-water stream is selected from the group consisting of a water-in-oil (W/O) stream, an oil-in-water (O/W) stream, and combinations thereof.

2. The method of claim 1, comprising using leonardite as a source of said humic acid.

3. The method of claim 1, further comprising the step of replacing said humic acid by an oxidizing agent, or replacing at least a portion of said humic acid by said oxidizing agent.

4. The method of claim 3, wherein said oxidizing agent is selected from the group consisting of sodium hypochlorite, calcium hypochlorite, and combinations thereof.

5. A method for separating an alkaline cation and a foulant from a water stream, said method comprising the steps of: (a) mixing said water stream with leonardite and an amine solvent to form a precipitate comprising said alkaline cation and said foulant in a precipitator unit; and (b) removing said precipitate by a filter, and recovering at least a portion of said amine solvent by a stripping unit to produce at least a treated water stream.

6. The method of claim 5, wherein step (a) further comprises the step of mixing said water stream with an oxidizing agent; wherein said oxidizing agent is selected from the group consisting of sodium hypochlorite, calcium hypochlorite, and combinations thereof.

7. The method of claim 5, wherein said alkaline cation is selected from the group consisting of magnesium, calcium, strontium, barium, radium, and combinations thereof; and wherein said alkaline cation is precipitated in the form of hydroxide.

8. The method of claim 5, wherein said foulant is selected from the group consisting of bromide, transition metals, sulfate, carbonates, radium decay series, silica, selenium, boron, and combinations thereof.

9. The method of claim 5, wherein said amine solvent is selected from the group consisting of isopropylamine, propylamine, dipropylamine, diisopropylamine, ethylamine, diethylamine, methylamine, dimethylamine, and combinations thereof.

10. A method for separating an alkaline cation from a water stream, said method comprising the steps of: (a) mixing said water stream with a sulfate source and an amine solvent to form a precipitate comprising said alkaline cation in a precipitator unit; and (b) removing said precipitate by a filter, and recovering at least a portion of said amine solvent by a stripping unit to produce at least a treated water stream.

11. The method of claim 10, wherein said alkaline cation is selected from the group consisting of barium, radium, and combinations thereof; and wherein said alkaline cation is precipitated in the form of sulfate.

12. The method of claim 10, wherein said sulfate source is a sulfate-rich stream, a sulfate-based compound, and combinations thereof.

13. The method of claim 12, wherein said sulfate-rich stream comprises mine drainage water, a spent stream from a flue gas scrubber, agricultural drainage water, an effluent stream from a wastewater treatment plant, a reject stream from an advanced wastewater treatment plant, and combinations thereof.

14. The method of claim 12, wherein said sulfate-based compound comprises magnesium sulfate, calcium sulfate, sodium sulfate, potassium sulfate, and combinations thereof.

15. The method of claim 10, wherein said amine solvent is selected from the group consisting of isopropyl amine, propyl amine, dipropylamine, diisopropylamine, ethylamine, diethylamine, methylamine, dimethylamine, and combinations thereof.

16. A method for separating an alkaline cation and bromide from a water stream, said method comprising the steps of: (a) mixing said water stream with an amine solvent and an oxidizing agent to form a precipitate comprising said alkaline cation and said bromide in a precipitator unit; and (b) removing said a precipitate by a filter, and recovering at least a portion of said amine solvent by a stripping unit to produce at least a treated water stream.

17. The method of claim 16, wherein said alkaline cation is magnesium; and wherein said magnesium is precipitated in the form of hydroxide.

18. The method of claim 16, wherein said amine solvent is selected from the group consisting of isopropylamine, propylamine, dipropylamine, diisopropylamine, ethylamine, diethylamine, methylamine, dimethylamine, and combinations thereof.

19. The method of claim 16, wherein said oxidizing agent is selected from the group consisting of sodium hypochlorite, calcium hypochlorite, and combinations thereof.

20. The method as in any one of claims 5, 10, or 16, further comprising feeding said treated water stream to a desalination train; wherein said desalination train comprises at least one heat exchanger, a plurality of flashing stages arranged in series, and at least one compression device; wherein said treated water stream to be desalinated passes through said heat exchanger and through said plurality of flashing stages in succession to heat the water to a vaporization temperature by maintaining said flashing stages at a progressively lower pressure in a downward direction; wherein said treated water stream is at least at a saturation temperature corresponding to the pressure in said flashing stage, and flows to a next succeeding flashing stage which is at a lower pressure, and the input into said next flashing stage is at a temperature higher than the saturation temperature corresponding to said lower pressure in said next flashing stage; wherein at a least a portion of said treated water stream flashes into vapor in each of said flashing stages; withdrawing said vapor from each of said flashing stages, and compressing at least a portion of said withdrawn vapor by said compression device and condensing the compressed vapor in said heat exchanger thereby producing a distillate stream; and wherein said treated water stream is heated before entering said first flashing stage of said desalination train; and discharging non-flashed water from said last flashing stage of said desalination train as a reject brine stream.

21. The method of claim 20, wherein said flashing stages comprise hydrophobic membranes.

22. The method of claim 20, wherein said flashing stages further comprise vapor-liquid separators, wherein said vapor-liquid separators comprise hydrophobic demister pads.

23. The method of claim 20, wherein said compression device is driven mechanically, thermally, and/or combinations thereof.

24. The method of claim 20, wherein said desalination train further comprises arranging said plurality of flashing stages in parallel to heat the water to a vaporization temperature by maintaining said flashing stages at a lower pressure; wherein said treated water stream is at least at a saturation temperature corresponding to the pressure in said flashing stages; wherein at a least a portion of said treated water stream flashes into vapor in each of said flashing stages; withdrawing said vapor from each of said flashing stages, and compressing at least a portion of said withdrawn vapor by said compression device, and condensing the compressed vapor in said heat exchanger thereby producing a distillate stream; and wherein said treated water stream is heated before entering said flashing stages of said desalination train; and discharging non-flashed water from said flashing stages of said desalination train as said reject brine stream.

25. A method for desalinating a treated water stream, said method comprising a brine forward (BF) desalination system; wherein said BF desalination system comprises a plurality of desalination trains arranged in series, in which each of said desalination train comprises at least a heat exchanger, a plurality of flashing stages arranges in series or in parallel, and at least a compression device; wherein said flashing stages comprise hydrophobic membranes; wherein said compression device is driven mechanically, thermally, and/or combinations thereof; wherein each of said desalination train produces a distillate stream and a reject brine stream; wherein said reject brine stream from each of said desalination trains with the exception of the last desalination train in said BF desalination system passes as a feed to a next succeeding desalination train, whereby each of said desalination train progressively possesses a higher level of total dissolved solids (TDS) than a preceding train, and wherein said reject brine stream from said last desalination train in said BF desalination system is discharged at a level not exceeding 250,000 mg/L of said TDS; whereby said BF desalination system is a multi-flashing system without supplying additional heat after said heat exchanger of each of said desalination trains; and providing a multi-concentration system without supplying additional treated water streams after passing through a first heat exchanger of said first desalination train.

\* \* \* \* \*